United States Patent [19]
Pinkus

[11] Patent Number: 5,855,915
[45] Date of Patent: Jan. 5, 1999

[54] TABLETS OR BIOLOGICALLY ACCEPTABLE IMPLANTS FOR LONG-TERM ANTIINFLAMMATORY DRUG RELEASE

[75] Inventor: A. George Pinkus, Robinson, Tex.

[73] Assignee: Baylor University, Waco, Tex.

[21] Appl. No.: 672,595

[22] Filed: Jun. 28, 1996

Related U.S. Application Data

[60] Provisional application No. 60/000,616 Jun. 30, 1995.

[51] Int. Cl.[6] ................................................. A61K 9/10
[52] U.S. Cl. ........................... 424/486; 424/426; 424/468
[58] Field of Search .............................. 514/772.2, 964; 424/426, 428, 468, 457, 486

[56] References Cited

U.S. PATENT DOCUMENTS

| | | | |
|---|---|---|---|
| 3,422,871 | 1/1969 | Schmitt et al. | 260/78.3 |
| 4,025,613 | 5/1977 | Guy et al. | 424/21 |
| 4,166,800 | 9/1979 | Fong | 252/316 |
| 4,308,251 | 12/1981 | Dunn et al. | 424/19 |
| 4,375,468 | 3/1983 | Dunn | 424/230 |
| 4,520,009 | 5/1985 | Dunn | 424/78 |
| 4,994,281 | 2/1991 | Muranishi et al. . | |
| 5,164,188 | 11/1992 | Wong . | |
| 5,206,030 | 4/1993 | Wheatley et al. | 424/490 |
| 5,206,386 | 4/1993 | Narayanan et al. | 548/551 |
| 5,324,519 | 6/1994 | Dunn . | |
| 5,447,725 | 9/1995 | Damani et al. . | |
| 5,449,382 | 9/1995 | Dayton . | |
| 5,458,888 | 10/1995 | Chen | 424/464 |
| 5,487,897 | 1/1996 | Polson et al. . | |
| 5,518,730 | 5/1996 | Fuisz | 424/426 |
| 5,543,156 | 8/1996 | Roorda et al. . | |
| 5,551,954 | 9/1996 | Buscemi et al. . | |

FOREIGN PATENT DOCUMENTS

| | | |
|---|---|---|
| 115986 | 8/1984 | European Pat. Off. . |
| 2473308 | 7/1981 | France . |
| 2539989 | 8/1984 | France . |
| 2001736 | 7/1970 | Germany . |
| 1917738 | 10/1970 | Germany . |
| 2149699 | 4/1972 | Germany . |
| 3346571 | 7/1985 | Germany . |
| 4121127 | 1/1993 | Germany . |
| 53-124607 | 10/1978 | Japan . |
| 54-154515 | 12/1979 | Japan . |
| 60-181029 | 9/1985 | Japan . |
| 4-360825 | 12/1992 | Japan . |
| 7-157439 | 6/1995 | Japan . |
| 1109425 | 4/1968 | United Kingdom . |
| WO 84/00004 | 1/1984 | WIPO . |
| WO 92/11845 | 7/1992 | WIPO . |
| WO 93/18755 | 9/1993 | WIPO . |
| WO 95/13799 | 5/1995 | WIPO . |

OTHER PUBLICATIONS

Yolles and Satori, "Erodible Matrices," In: *Controlled Release Technologies*, Chap. 1, pp. 2–6, 1980.

Anonymous, "Sustained Released Compositions," *Res Discl*, 259:567–570, 1985.

Asch et al., "Studies of a Controlled–Release Microcapsule Formulation of an LH–RH Agonist (D–Trp–6–LH–RH) in the Rhesus Monkey Menstrual Cycle," *Int J Fertil*, 30(2):19–26, 1985.

Bechgaard and Pedersen, "Rate of Drug Release from Intact and subdivided Controlled–Release Tablets," *Pharmaceuticals*, 86:325, Abstract No. 195155k, 1977.

Blume et al., "Bioavailability of Acetylsalicylic Acid Based Analgesics. Bioavailability of Two Immediate–Release ASA Tablet Formulations," *Pharm Ztg Wiss*, 6:59–64, 1993.

(List continued on next page.)

*Primary Examiner*—Edward J. Webman
*Attorney, Agent, or Firm*—Arnold White & Durkee

[57] ABSTRACT

The present invention involves an aspirin/polyglycolide complex, its preparation and use. The complex provides a stable aspirin source, slowly releasing aspirin by dissociation or during polyglycolide degradation in vivo.

7 Claims, 6 Drawing Sheets

OTHER PUBLICATIONS

Blume et al., Eds., "Controlled/Modified Release Products. Recommendation in Support of EC–Guidelines," Stuttgart, Ger: Wissenschaftliche Verlagsgesellschaft mbH, 1991.

Brantmark et al., "Bioavailability of Acetylsalicylic Acid and salicyclic Acid from Rapid–and slow–Release Formulations and in Combination with Dipyridamol," *Eur J Clin Pharmacol*, 22:309–214, 1982.

Casadio et al., "Acetylsalicylic Acid–Containing Drugs with Sustained Release," *Pharmaceuticals*, 77:303, Abstract No. 9593t, 1972.

Chapman et al., "Sustained Release of Drugs in Certain Drug–Resin Complexes as Judged by Urinary Excretion Rates," *Can Med Assoc J*, 81:470–476, 1959.

Charles, "Sustained–Release Aspirin," *Chem. Abstr*, 100:362, Abstract No. 126906b, 1984.

Charman et al., "Biopharmaceutical Characterisation of a Low–dose (75 mg) Controlled–Release Aspirin Formulation," *Br. J. Clin Pharmacol*, 36:470–473, 1993.

Chen, "Controlled–Release Tablets Comprising Coated cores and PEG Coatings," *Chem. Abstr*, 123:712, 1995.

Chick, "Programmed–Release Compositions Containing Acetylsalicyclic Acid and Dihydroergotamine," *Pharmaceuticals*, 101:313, Abstract No. 235613v, 1984.

Chick, "Programmed–Release Pharmaceuticals Containing Acetylsalicylic Acid," *Chem Abstr*, 101:356, Abstract No. 157704j, 1984.

Choudhury and Mitra, "Kinetics of Aspirin Hydrolysis and stabilization in the Presence of 2–Hydroxypropyl–β–Cyclodextin," *Pharm. Res.*, 10(1):156–159, 1993.

Chowdary and Rao, "Studies on a New technique of Microencapsulation: Part V. Microencapsulation of Aspirin by Ethylcellulose," *Indian Drugs*, 22(9):479–481, 1985.

Deasy and Murtagh, "Controlled Release Antiplatelet Product Containing Dipyridamole and Aspirin," *Chem Abstr*, 119:556, Abstract No. 233957h, 1993.

Dong and Rogers, "Acacia–Gelatin Microencapsulated Liposomes: Preparation, Stability, and Release of Acetylsalicylic Acid," *Pharm Res*, 10(1):141–146, 1993.

Dunn and Lampard, "Pharmaceutical Composition with a Prolonged Effect," *Chem Abstr*, 95:381–381, Abstract No. 225675k, 1981.

Froemming and Topaloglu, "Influence of Ethanol on the In Vitro and In Vivo Drug Release from Some Sustained Release Tablets," *Chem Abstr*, Abstract No. 84:99089e, 1976.

Frömming and Topaloglu, "Beeinflussung der In–vitro–und In–vivo–Pharmakonfreisetzung Aus Einigen Peroralen Depotformen unter Äthanolbelastung," *Arzneim–Forsch*, 25:1958–1964, 1975 (See Ref C19 for English Abstract).

Fujimoto, "Aspirin–Dextrin Inclusion Compounds," *Chem Abstr*, 90:286, Abstract No. 76581u, 1979.

Gaudy et al., "Controlled–Release Acetylsalicylic Acid Hydrophilic Matrix Tablets," *Congr. Int. Technol. Pharm 6th*, 3:365–372, 1992.

Gilding and Reed, "Biodegradable Polymers for Use in Surgery—Polyglycolic/Poly(Actic Acid) Homo–and Copolymers: 1," *Polymer*, 20:1459–1464, 1979.

Ginde and Gupta, "In Vitro Chemical Degradation of Poly(Glycolic Acid) Pellets and Fibers," *J of App Poly Sci*, 33:2411–2429, 1987.

Habib et al., "Effect of Certain Additives on the Diffusion Characteristics of Aspirin, Salicylamide and Phenacetin Through A Cellophane Membrane. II. Effect of Aliphatic Acids and Polyethylene Glycol.," *Chem Abstr*, Abstract No. 104:174526g, 1986.

Hariharan and Pinkus, "Useful NMR Solvent Mixture for Polyesters: Trifluoroacetic Acid–d/Chloroform–d," *Polymer Bulletin*, 30:91–95, 1993.

Hosoi et al., "Use of Porous Particles for Preparation of Capsules Containing Aspirin and Drug Release properties," *Chem Abstr*, Abstract No. 103:166045p, 1985.

Hutchinson and Furr, "Biodegradable Polymers for the sustained Release of Peptides," *Biochemical Society Trans*, 13:520–523, 1985.

Ikada and Gen, "Sustained–Release Pharmaceuticals Containing Lactic Acid Polymers," *Chem Abstr*, 104:384, Abstract No. 39744m, 1986.

Ishii et al., "Sustained–Release Preparations for Bone Implants," *Pharmaceuticals*, 123:671, Abstract No. 179584b, 1995.

Karahalios et al., "Comparative Bioavailability of Sustained–Release and Uncoated Aspiring Tablets," *Am J Hosp Pharm.*, 38;1754–1756, 1981.

Kawashima et al., "Preparation of a Prolonged Release Tablet of Aspirin with Chitosan," *Chem. Pharm. Bull*, 33(5)2107–2113, 1985.

Khan and Alam, "The In–Vitro Study of Sustained Release Aspirin Tablet with Polyethylene Resin as Insoluble Matrix," *Pakistan J. Sci. Ind. Res.*, 23(6):283–286, 1980.

Kitajima et al., "Encapsulation with Polymeric Materials," *Plastics Fabrication and Uses*, 73:43, Abstract No. 78221z, 1970.

Kydonieus, Ed., "Treatise on Controlled Drug Delivery," New York: Marcel Dekker, Inc., 1991.

Li et al, "Copolymer of 1–(acetylsalicyloyloxy)ethyl Methacrylate and Its Hydrolysis," *Chem Abstrs*, Abstract No. 102:190971n, 1985.

Li et al., "Sucralfate as a Bioadhesive Gastric Intestinal Retention System: Preliminary Evaluation," *Drug Development and Industrial Pharmacy*, 19(19) 2519–2537, 1993.

Linhardt, "Biodegradable Polymers for controlled Release of Drugs," *Controlled Release of Drugs*, Rosoff, Ed., New York: VCH Publishers, Chapter 2, p. 82, 1989.

Lobeck and Spigiel, "Bioavailability of Sustained–Release Aspirin Preparations," *Clinical Pharmacy*,5:236–238, 1986.

Molloy et al., "Method for Production of Solid Pharmaceutical Dosage Forms," *Chem Abstr*, 118:352, Abstract No. 27464w, 1993.

Murakami et al., "Manufacture of Sustained–Release Pharmaceutical Microspheres," *Pharmaceuticals*, 118:459, Abstract No. 154585k, 1993.

Naplatanova et al., "Depo–acetysal Tablets," *Chem Abstrs,* Abstract No. 76:158288d, 1972.

Nikolayev and Gebre–Mariam, "Preparation and Bioavailability Studies of Aspirin Ethyl Cellulose Microcapsules," *Indian Drugs*, 30(8):392–397, 1993.

Pinkus and Subramanyam, "New High–Yield, One–Step Synthesis of Polyglycolide from Haloacetic Acids," *J of Polymer Science: Polymer Chemistry Edition*, 22:1131–1140, 1984.

Plaizier–Vercammen and van den Bossche, "Evaluation of the Tabletting Properties of a New Exipient for Direct Compression," *Pharm Ind*, 54:973–977, 1992.

Ramstack et al., "Preparation of Biodegradable Microparticles Containing a Biologically active Agent," *Chem Abstr*, 123:664, Abstract No. 179481r, 1995.

Rehders et al., Plasma Salicylate Levels and Platelet Function After Acute and Chronic Administration of Slow–Release Acetylsalicylic Acid (Monobeltin), *Eur J Clin Pharmacol*, 27:638–687, 1985.

Rettenmaier, "Coated Cellulose Particles for Direct Dry Drug Tabetling," *Pharmaceuticals*, 118:499, Abstract No. 132173y, 1993.

Roberts et al., "Inhibition of Platelet Function by a Controlled Release Acetylsalicylic Acid Formulation–Single and Chronic Dosing Studies," *Chem Abstrs*, Abstract No. 102:12274e, 1985.

Roseman and Mansdorf, Eds., "Controlled Release Delivery Systems," New York: Marcel Dekker, Inc., 1983.

Sakauchi and Kawakami, "Sustained–Release Pharmaceuticals," *Chem Abstr*, 92:334, Abstract No. 203591r, 1980.

Schoen et al., "Embedding or encapsulating Solid or Liquid Substances in Polymers Containing Carboxyl or Carboxylate Groups," *Plastics Fabrication and Uses*, 74:35, Abstract No. 4375b, 1971.

Sharma and Paul, "Poly Vinylalcohol Dialysis Membranes: Permeability Changes Due to Aspirin Release," *Polym Mater Sci Eng*, 66;495–496, 1992.

Shell, "Alkyl–substituted Cellulose–Based Sustained–Release Oral Drug Dosage Forms," *Pharmaceuticals*, 119:467, Abstract No. 256550j, 1993.

Stivic and Senjkovic, "Ion Exchangers and Sustained Release Action of Drugs," *Chem Abstrs*, Abstract No. 82:116048u, 1975.

Stivic and Senjkovic, "Izmjenjivaci Iona i Produzeno Djelovanje Lijekova," *Acta Pharm. Jugoslav*, 24:249–258, 1974 (See Ref. C55 for English Abstract).

Streuff and Puetter, "Slow–Release Acetylsalicyclic Acid Oral Formulations," *Chem Abstr*, 103:362, Abstract No. 129080a, 1985.

Struszczyk and Boldowicz, "Conception of Microcrystalline Cellulose Application as Polymeric Carriers for the Controlled Release of the Acetylsalicylic Acid," *Cellulose Chem and Tech*, 20:201–207, 1986.

Super et al., "Incorporation of Salicylates into Poly(L–lactide)," *Polymer Bulletin*,32:509–515, 1994.

Tanner and Gardner, "Polymeric Coating of Aspirin," *Chem Abstr*, 68:10436, Abstract No. 107899f, 1968.

Tarcha, ed., "Polymers for Controlled Drug Delivery," Boca Raton, FL: CRC Press, 1991.

Thanoo et al., "Controlled Release of Oral Drugs from Cross–Linked Polyvinyl Alcohol Microspheres," *J. Pharm. Pharmacol.*, 45:16–20, 1993.

Thanoo et al. "Oral Sustained–Release Drug Delivery Systems Using Polycarbonate Microspheres Capable of Floating on the Gastric Fluid," *J. Pharm. Pharmacol.*, 45:21–24, 1993.

Torrado et al. "In Vitro' Drug Release of AAS Matrix Tablets," *Proceed Intem. Symp. Control. Rel. Bioact. Mater.*, 20:370–371, 1993.

Tu et al., "Sustained–Release Aspirin Tablets," *Chem Abstrs*, Abstract No. 105:102450a, 1986.

Wang et al., "A Study of Aspirin Slow–Release Dosage Form (III)," *Chem Abstrs*, Abstract No. 119:80099c, 1993.

Wilson et al., "Pharmacokinetics and In Vivo Scintigraphic Monitoring of a Sustained Release Acetylsalicyclic Acid Formulation," *Int'l J of Pharmaceutics*, 18:1–8, 1984.

Yanaihara et al., Pharmacokinetics of Acetylsalicyclic Acid and Salicyclic Acid from Slow–Release Formulations of Aspirin in Healthy Japanese Volunteers, *Chem Abstrs*, Abstract No. 104:10520z, 1986.

Yanaihara et al., "Pharmacokinetics of Acetylsalicyclic Acid and Salicylic Acid from Slow–Release formulations of Aspirin in Healthy Japanese Volunteers," *Rinsho Yakuri*, 16:589–596, 1985.

TABLETS OR BIOLOGICALLY ACCEPTABLE IMPLANTS FOR LONG-TERM ANTIINFLAMMATORY DRUG RELEASE

This is a continuation-in-part of provisional U.S. Ser. No. 60/000,616, filed Jun. 30, 1995, priority of which is elected. The present invention relates to formulations for the storage and/or slow release of biologically active carboxylates. Incorporation, e.g., of nonsteroidal anti-inflammatory agents into a slowly hydrolysable polyester is included.

BACKGROUND OF THE INVENTION

Because of the irregularly timed therapeutic effects of drugs as administered via tablets, powders, or injections, controlled time-release has always been a desirable goal. Many methods for accomplishing this have been proposed (Blume; Kydonieus; Rosoff; Roseman et al.). Disadvantages of most of these methods include: (1) Introduction of extraneous non-degradable material; (2) Heterogeneity of drug/material composite. (3) Incompatibility with living tissues. These disadvantages apply to aspirin and related drugs. Although the use of time-tested biodegradable matrices such as polyglycolide (Gilding et al.), the first synthetic absorbable suture material (Schmitt et al.), would appear to be well-suited for such uses, polyglycolide has not been used because ". . . its low solubility in common solvents has made the formulation of composites difficult and its use in drug delivery problematic." (Linhardt; Yoles et al.). However, polylactide and poly(lactide-co-glycolide) which are soluble under certain circumstances have been used to some extent (Fong, Asch et al., Hutchinson et al., Ikada et al., Murakami, Ramstack et al.).

Reported examples of the controlled release relating to aspirin follow. Evaluation of sustained release of acetylsalicylic acid complexed with an ion-exchange resin was made by comparing urinary excretion rates with that of acetylsalicylic acid alone. It was concluded that more critical and quantitative evaluation of resinate drug medication for more effective in vitro tests was needed (Chapman et al., 1959).

Slow dissolution may be provided by coating the aspirin tablet, or crystals from which it is formed, with poly (salicylic anhydride) [H—$(OC_6H_4CO)_n$OH where n is 2–6]. Coating can be effected by heating the tablets or crystals for 20 min. at 120° C. or by treating them with a solution of the polymer in a solvent, preferably by dipping the tablets in a 1% solution of polymer in benzene followed by drying and successive dippings, 5 in all. Relative solubility of differently prepared tablets in 0.1N HCl stirred at 200 rpm at 37° C. was determined (Tanner et al., 1968).

Aspirin or pancreatin may be encapsulated by dispersing them in solutions of polycarbonates, poly(vinyl chloride), cornstarch, polystyrene, cellulose acetate phthalate, poly (acrylic acid), or shellac, in organic solvents, dispersing the dispersions formed in aqueous solutions of inorganic salts, e.g. ammonium sulfate, disodium hydrogen phosphate, sodium chloride, or calcium chloride, and removing the organic solvent. Thus, a dispersion of 1 g. of pancreatin in a solution of 2 g. of aspirin in 20 g. of acetone was added to 60 g. of ammonium sulfate in 100 g. of water at 15° C. and heated 2 h at 30° C. to give capsules of 1.5–2 mm. diameter containing 30% enzyme, and soluble in intestinal juice (Kitajima et al., 1970).

Encapsulation of acetylsalicylic acid in Na CM (carboxymethyl)-cellulose, a maleic anhydride-styrene copolymer, or a methacrylic acid-methyl methacrylate copolymer was accomplished by spraying a dilute solution of the $CO_2$H-containing polymer and the oil, etc. into a dilute aqueous aluminum sulfate solution. For example, an emulsion of 5:14 oil and 1% Na-CM-cellulose was sprayed into a 0.1M aluminum sulfate solution to prepare capsules having an average diameter of 1.2 mm. (Schoen et al., 1970).

Tablets, capsules, and gels were prepared containing granules of acetylsalicylic acid, ethoxyethyl cellulose, and dimethylpolysiloxane, which resulted in sustained release of aspirin. Thus, 1000 g. of powdered acetylsalicylic acid of 0.177 mm. diameter was added to 70 g. of Ethocel 20 (ethoxyethyl cellulose, ethoxy content 12%) in 300 mL in 1:1 toluene-dichloromethane. dimethylpolysiloxane (30 g.) in 90 mL of toluene was added and the solvent evaporated; the formed paste was extruded to give particles of 1 mm. diameter, which were hardened and dried. The granules obtained were filled into gelatin capsules. Tablets were prepared containing the above granules 0.715, starch 0.040, glycerol palmitate stearate 0.030, talcum 0.005, and microcrystalline cellulose 0.010 g. (Casadio et al., 1972).

A slow-release acetylsalicylic acid preparation, maintaining a steady level of 5–6 mg. % of acetylsalicylic acid in the plasma of rabbits throughout 24 hr. after oral administration. Administration at 100 mg./kg. was recommended for further clinical trial. Composition of the specific preparation was not given (Naplatanova et al., 1972).

Particle size and total exchange capacity were examined for 22 cation and anion exchangers used as binders for drugs with sustained-release action. The sustained-release effect was examined with standard preparations containing acetylsalicylic acid by the half-change method. Release of aspirin was very slow and incomplete even after 6 h. Ion exchangers for preparing sustained-release preparations should be used discriminately (Stivic et al., 1974).

In vitro, EtOH increased the solubility of sustained release tablets of acetylsalicylic acid made with Eudragit retard-1, Methocel 65, or carbopol 934 but inhibited that of preparations made with Precirol (Froemming, 1975).

Intact and subdivided controlled-release tablets of acetylsalicylic acid showed no significant difference in cumulative release in vitro (Bechgaard et al., 1977).

Timed-release aspirin tablets were prepared by coating aspirin particles with cellulose acetate phthalate and a plasticizer in an organic solvent and pressing together layers of this coated aspirin and uncoated aspirin. E.g., 65 kg. of acetylsalicylic acid were treated with 2 gal. of a coating solution containing cellulose acetate phthalate 6, dichloromethane 17, diethyl phthalate 1.2, and acetone 15 kg, the coated aspirin granules dried, and ground to 20 mesh. Tablets containing 6 mg. of the above coated aspirin and 4 mg. of uncoated aspirin mixed with starch were pressed in a conventional 2-layer press. The uncoated layer dissolved readily in simulated gastric juice while the coated layer dissolved little in the simulated gastric juice but completely in simulated intestinal juice (Guy et al., 1977).

Aspirin was treated with dextrins to form aspirin-dextrin inclusion compounds with no side effects. Thus, tablets were prepared containing the powdered inclusions compound 2000, crystalline cellulose 500, and Mg stearate 30 g. The inclusion compounds were sustained-release compared to aspirin alone as reflected by blood aspirin concentrations in rabbits (Fujimoto, 1978).

Sustained-release pharmaceuticals were manufactured by adsorption of drugs onto bead-shaped active charcoal. Thus, 30 g. aspirin was dissolved in EtOH, the solution mixed with 100 g. bead-shaped charcoal to give the adsorbed aspirin (Sakauchi et al., 1979). Sustained-release aspirin tablets were also evaluated by using polyethylene as insoluble matrix and ethyl cellulose binder in different proportions (Khan, 1980).

Microspheres with a core material (drug) encapsulated with a polymer coating were prepared by dissolving the polymer in a solvent in which the drug is insoluble and polymer precipitated by phase separation to encapsulate the core. Temperature of the system was −40° to −100° C. A solution of 1.0 g poly(DL-lactic acid) in 50 mL toluene was cooled to −65° C. and micronized Mellaril pamoate (0.5 g) was dispersed in the solution. Isopropyl alcohol (150 mL) was added dropwise to the solution and the microcapsules settled. The product was washed twice with heptane and dried to give spherical microcapsules with 25–50 m diameter (Fong, 1980).

Plasma salicylate concentrations during multiple-doses of an uncoated and a sustained-release aspirin preparation were compared. Sustained-release aspirin preparations produced plasma salicylate concentrations comparable to those obtained with uncoated aspirin tablets administered more frequently (Karahalios et al., 1981).

Antiinflammatory tablets with retarded action are prepared containing the active ingredient, a regulator for release of active ingredient, and an erosion promoter in relative proportions according to the equation: CF=CA/(1/CS), where CF=crit. factor; CA=amt. of active ingredient (mg.); CS=amt. of erosion promoter divided by the amt. of release regulator (mg/tablet). Thus, tablets containing 650 mg. of acetylsalicylic acid were prepared from granulated mixtures of acetylsalicylic acid 4375, cellulose acetate phthalate 67.3, and corn starch 225.5 g. Retarded release of aspirin was confirmed by determination in serum. Tablets of ibuprofen and flurbiprofen with retarded action were prepared similarly (Dunn, Lampard, 1981).

Improved tablet formulations consist of effective amounts of active therapeutic agents such as aspirin, a release-controlling agent, and an erosion promoting agent in relative amounts to provide a critically factor of <450. The proportions of release-controlling and erosion-promoting agents are 0.8–1.6 and 1.0–7.5 wt. %/tablet, resp. The tablets show zero order release in vitro and approx. zero order absorption in vivo. When aspirin is the therapeutic agent, the tablets can be administered twice a day for prolonged therapeutic effect and their use is not characterized by extreme gastro irritation. A solution of cellulose acetate phthalate 67.3 g. in EtOH 625, and dichloromethane 175 mL was added with stirring to a dry powdered mix of aspirin 4.38 and corn starch 0.23 kg. in 30 s, and the mixing further continued for 4 min. at higher speed to promote granulation. The wet granular mass was air dried and compressed to produce tablets containing 650 mg. of aspirin with a hardness of 8–10 kp. These tablets show enhanced stability on storage (Dunn, Lampard, 1981).

Plasma salicylate concentrations during multiple-doses of an uncoated and a sustained-release aspirin preparation were compared. Sustained-release aspirin preparations produced plasma salicylate concentrations comparable to those obtained with uncoated aspirin tablets administered more frequently (Karahalios et al., 1981).

In order to compare bioavailability of unchanged acetylsalicylic acid from rapid and slow-release formulations, single-dose concentration profiles of acetylsalicylic acid and salicylic acid were studied in healthy volunteers following intake of two rapid-release (conventional and effervescent tablets) and three slow-release (microencapsulated tablets and in capsules, and enteric-coated tablets) formulations of acetylsalicylic acid, and one slow-release formulation of Na salicylate (Brantmark et al., 1982).

Sustained-release aspirin tablets for treatment of arthritis and menstrual cramps with reduced side effects were prepared comprising aspirin, hydrogenated vegetable oil and a sugar. Thus, tablets containing aspirin (80 mesh) 650, hydrogenated cottonseed oil 30, lactose 15, hydroxypropyl Me cellulose 4, and talc 3 g. (EtOH and 40 mL dichlormethane were added during formulation). Tablets could be administered once or twice daily (Dunn, 1983).

A sustained-release aspirin providing $\geq 8$ h of continuous delivery consists of 1.5–15 parts of ethyl cellulose and 1 part of hydroxypropyl cellulose. The coated capsules may be encapsulated for administration or can be packaged in a sealed pouch for mixing with food or beverage. Thus, 700 g of aspirin crystals were coated in an air suspension column with a solution of 29.4 g. of ethyl cellulose and 7.4 g. of hydroxypropyl cellulose in 92 mL of methanol sprayed at 60 mL/min. Inlet air temperature was 60° C. (Charles, 1983).

Programmed-release pharmaceuticals containing acetylsalicylic acid were prepared from poly(methacrylic acid). Thus, a unitary formulation was prepared containing aspirin 330, sucrose 38, corn starch 10, talc 20, povidone 37, poly(methacrylic acid) 5.7, and ethyl phthalate 2 mg. (Chick, 1984).

Programmed-release compositions consist of dihydroergotamine aspirin and acetylsalicylic acid encapsulated in poly(methacrylic acid) or its ester. Thus, capsules were prepared, each methanesulfonate (immediate release) 1.5, dihydroergotamine aspirin methanesulfonate (programmed-release) 3.5, acetylsalicylic acid 40, sucrose 80, corn starch 22, talc 45, lactose 21.5, povidone 72, poly(methacrylic acid 11, and ethyl phthalate 3 mg. Dosage was 2 capsules/day to be administered one in the morning and one in the evening (Chick, 1984).

1-(Acetylsalicyloyloxy)ethyl methacrylate-methacrylic acid copolymer was prepared and hydrolyzed in dioxane-water at acidic or alkaline pH at 37° or 60° C. The main hydrolysis product was aspirin and the minor hydrolysis product was salicylic acid. The hydrolysis rate increased with increasing mole fraction of methacrylic acid in the copolymer and increasing pH values of the hydrolysis medium. Thus, the copolymer may be used as controlled-release aspirin preparations (Li, F. et al., 1984).

The extent to which a controlled-release acetylsalicylic acid formulation inhibited platelet function was evaluated in single and chronic dosing studies (Roberts et al., 1984).

Effect of succinic, citric, and tartaric acids and polyethylene glycol 1500, 2000, 4000, and 6000 on diffusion rate of aspirin, salicylamide, and phenacetin through a standard cellophane membrane was studied (Habib, 1984).

In vivo dissolution and pharmacokinetics of a sustained-release aspirin formulation labeled with [$^{99m}$Tc] diethylenetriaminepentaacetic acid was monitored in 5 subjects by use of scintigraphy and analysis of blood and urine samples. Data confirmed sustained release properties of the cellulose acetate phthalate-containing formulation (Wilson, 1984).

Effect of succinic, citric, and tartaric acids and polyethylene glycol 1500, 2000, 4000, and 6000 on diffusion rate of aspirin, salicylamide, and phenacetin through a standard cellophane membrane was studied (Habib, 1984).

Aspirin was microencapsulated by emulsifying ethyl cellulose solution containing aspirin in an immiscible liquid medium (paraffin) followed by coacervation by adding water. The microcapsules were discrete, spherical, and free flowing. Release from the microcapsules was slow and spread over 5 h. (Chowdary et al., 1985).

Aspirin compositions are prepared for a sustained release and lasting antiinflammatory and analgesic effect. Compositions containing aspirin 88% and starch paste 12–30% (wt.) are easily formulated into dosage forms such as tablets and hard gelatin capsules at low cost. Thus, tablets containing 500 mg. aspirin and 6 different amounts of starch paste (60–100 mg.) and the appropriate amount of starch to give a weight of 600 mg./tablet were prepared (Streuff, 1985).

A compressed tablet contains an active drug of a fine particle size, water-soluble hydroxypropyl methyl cellulose (HPMC) with a hydroxypropyl substitution of 7–12 wt. %. MeO substitution of ~28–30 wt. % and a no. av. mol. wt. of $\geq 15,000$. The HPMC composition is sufficiently fine so that a tablet formulated from it can delay drug release longer than a similar composition containing an identical chemical but a coarser HPMC composition. A 780 mg. tablet containing aspirin 82.6, Methocel E-50 (HPMC) 16.5 (ball milled so that 95% HPMC particles pass through a 100 mesh screen), and Mg stearate 0.9% was compacted at 3000 lb in a 0.5 in. concave punch. Aspirin showed delayed release from this tablet up to 9 h. whereas the release was complete in 1 h. from a similar tablet composition prepared using HPMC which was not ball milled and 84% of the particles failed to pass through 100 mesh screen (Anon, 1985).

Effects on ovulation and hormonal profile during rhesus monkey menstrual cycle of a system that continuously delivers a potent agonist of LH-RH-Trp-6-LH-RH) encapsulated in poly([DL-lactide-co-glycolide)] were studied (Asch et al., 1985).

The relationship between antiplatelet effects and pharmacokinetics of a slow release formulation of acetylsalicylic acid was investigated (Rehders et al., 1985). A sustained-release aspirin tablet formulation for production in large batches comprises aspirin 85–95, microcrystalline cellulose 1.5–5, cellulose acetate phthalate 1–10, plasticizer 0.75–4.0, diluent 0.75–5.0, and lubricant 0.5–2.0%. Thus, a formulation for aspirin tablets (650 mg aspirin) contained 89.0, Avicel 1.0 wt. %, acetone 2000 mL, and dichloromethane 1000 mL (Dunn, 1985).

Polymer-coated porous particles containing aspirin were prepared and the rate of aspirin release was studied. Impregnation of aspirin was carried out by postgraft polymerization where methyl methacrylate or methacrylic acid was treated with porous particles, preirradiated with gamma-rays from $^{60}$Co in the presence of aspirin. Release of aspirin from modified particles was tested with 50% methanol solution and (or) pH 5.2 buffer solution of acetic acid. The amount of aspirin released from capsules increased with time and reached a constant value after 140 h. The amount of aspirin absorbed in porous particles increased with graft polymerization. Diffusion of aspirin through polymer matrix was the rate limiting step (Hosoi et al., 1985).

Sustained-release biodegradable delivery systems based on a polyester such as poly(DL-lactide) and poly(DL-lactide-co-glycolide) were developed. Release of the peptide Zoladex was studied both in vitro and in vivo (Hutchinson et al., 1985).

A prolonged-release tablet of aspirin was prepared by compressing aspirin and agglomerating by massing it with an acetic acid solution of chitosan (Kawashima et al., 1985).

Acetylsalicylic acid and salicylic acid concentrations in plasma were determined by HPLC in healthy male Japanese volunteers after single oral administrations of two different aspirin formulations, enteric coated granules (Minimax) and a slow-release tablet (Verin)(650 or 1300 mg.)(Yanaihara et al., 1985).

Sustained-release pharmaceuticals have been prepared by mixing lactic acid polymer or copolymer (mol. wt. 2,000–20,000) with drugs. These formulations were thought especially suitable for drugs unstable to heat. Thus, L-lactic acid polymer (mol. wt. 16,000) was kept at 80° C., mixed with 600,000 units urokinase and made into pills. Pills placed in saline slowly released urokinase over a one month period (Ikada et al., 1985).

Total mean aspirin recovery from urine of humans ingesting three slow-release aspirin formulations, Verin 650 mg., Zorpin 800 mg., or Measurin 650 mg., was similar to that in humans ingesting regular aspirin preparations; no differences were found among the products (Lobeck et al., 1986).

Therapeutic aspirin plasma levels were obtained from sustained-release aspirin tablets in 2 h. The aspirin plasma level was maintained at >30 mg/mL for $\leq 10$ h with the tablets (Tu, 1986).

Cellulose (microcryst.) was used as a carrier to prepare controlled-release pharmaceuticals. Acetylsalicylic acid was used as the model drug. Lyophilization produced a drug form with delayed-release properties (Struszczyl et al., 1986).

Solid pharmaceuticals were prepared by mixing finely divided particles or granules containing a drug, excipients, amorphous coating polymers, and plasticizers and compressing them into tablets. Thus, a water dispersible formulation of Aquateric 85 g., glyceryl stearate 15 g. and Mg stearate 0.1 g (as a lubricant) was mixed and used to encapsulate aspirin tablets (350 mg). The tablet was heated at 80°–90° C. for 15–20 min. to allow the polymer molecules to fuse together to form a continuous film (Molloy et al., 1991).

Membranes with 0.768 mg. of aspirin per cm. may be used for applications as dialysis membranes with enhanced blood compatibility and improved solute permeability (Sharma et al., 1992).

Tabletting characteristics of the excipient Ludipress (a mixture of lactose monohydrate with Kolidons 30 and CL) were investigated for directly compressed acetylsalicylic acid and phenobarbital tablets. Only low compressive forces were required although addition of a lubricant was necessary. Binding properties of acetylsalicylic acid were superior to those of microcrystalline cellulose. Drug release profiles from such formulations were sigmoid in shape and best interpreted by 1st order kinetics (Plaizier-Vercammen et al., 1992).

Matrix tablets containing acetylsalicylic acid capable of maintaining a blood platelet aggregation inhibitory effect for 8 h. were prepared by wet granulation. Substituted celluloses were used as excipients. The best dissolution profile was obtained when the concentration of the polymers did not exceed 5% (Gaudy et al., 1992).

A physiologically active substance (e.g. insulin-like growth factor) or its aqueous solution is mixed with poly-lactides (e.g., poly-L-lactic acid) solution and then with a crystallization medium (e.g., EtOH) to form microspheres for sustained-release without initial burst phenomenon (Murakami, 1992).

An improved controlled-release oral dosage form of dipy-ridamole and aspirin containing optimal dosage of both drugs was developed (Deasy et al., 1993). Complexation of aspirin with 2-hydroxypropyl b-cyclodextrin (HPbCD) increased the solubility and stability of the drug (Choudhury et al., 1993).

Liposomes of dipalmitoylphosphatidylcholine containing acetylsalicylic acid were microencapsulated by Acacia-gelatin using the complex coacervation technique as a potential oral drug delivery system (Dong et al., 1993).

Sustained-release, N-substituted pyrrolidone esters (substituent=ester moiety of a biologically active medicinal carboxylic acid or aminocarboxylic acid) provide a vehicle for dermal penetration and sustained release of the pharmaceutical by hydrolysis. Thus, 2-acetylsalicylic acid was condensed with N-(chloromethyl)-2-pyrrolidone to give an ester (Narayanan et al., 1993).

Ethyl cellulose-walled aspirin microcapsules were compressed into tablets or filled into hard capsules. Drug availabilities from these dosage forms were compared with those of conventional aspirin tablets. Studies in rabbits showed that constant plasma concentration of the drug was sustained for about 8–10 h. and pharmacokinetics of microencapsulated aspirin can be described by a one compartment open model. Comparison of in vitro drug release and in vivo drug availability showed that there is a strong correlation between dissolution and absorption for the first 6 h. for microencapsulated aspirin from tablets and hard capsules (Nikolayev et al., 1993).

Sustained-release oral dosage forms, e.g. tablets containing alkyl-substituted cellulose derivatives were described. Once the tablets disintegrate in the stomach to disperse the particles, they absorb water and swell, thus their retention in the stomach was enhanced. Hydroxypropylcellulose and aspirin of various proportions were mixed and compressed into 3 mm. diameter cylindrical pellets. Cumulative release of aspirin was monitored in simulated gastric fluid over a period of 7 h. Aspirin release was steady as compared to conventional tablets which released >90% within 0.5 h. (Shell, 1993).

Two polymers (Eudragit RS 100 and ethyl cellulose) were used in design and preparation of aspirin slow-release dosage forms by the Wurster process. Physical properties, dissolution, stability, and animal studies were determined. Microcapsule formulations using ethyl cellulose were more stable than Eudragit RS 100 and showed slow-release characteristics (Wang et al., 1993).

A water-dispersible, particulate film-forming composition for pharmaceuticals comprising cellulose acetate, a pigment, a plasticizer, and a surfactant. Aspirin tablets were coated with a dispersion containing cellulose acetate, $TiO_2$, dioctyl Na sulfosuccinate, and PEG-400. The coated tablets stored for 1 mo. at 80% humidity and 45° C. showed no sign of significant changes as compared with controls containing HPMC which exhibited severe physical instability, odor, and discoloration (Wheatley et al., 1993).

Matrix tablets of acetylsalicylic acid were produced by compression of acetylsalicylic acid coated pellets with acrylic resins (Eudragit RS). The drug release profile of acetylsalicylic acid pellets after compression with different excipients (microcrystalline cellulose, starch, and dextrose monohydrate) was studied (Torrado et al., 1993).

A prototype formulation of a gastric intestinal retention system was successfully developed. A matrix tablet containing sucralfate, Methocel E4M, and the appropriate type of drug powder, granules or pellets was prepared using Carver Press. Three different formulations were evaluated using three different drug entities, namely theophylline sustained release pellets, aspirin granules, and antacid powder. Tablets of these formulations showed remarkable adhesive characteristics onto the glass vessel in acidic medium up to at least 8 h. All three formulations exhibited sustained release in vitro dissolution profiles (Li, et al., 1993).

Release of aspirin from a 75 mg. controlled-release formulation, designed to inhibit maximally thromboxane $A_2$ production while sparing stimulated prostacyclin biosynthesis, was characterized in healthy subjects. The calculated in vivo release rate of aspirin matched the design goal of approx. 10 mg$^{-1}$. The $C_{max}$ of aspirin associated with the controlled-release formulation was lowered 15-fold relative to a solution formulation of the same dose. Bioavailability of aspirin (based on salicylate concentrations) from the controlled release formulation was approx. 90% relative to the solution and drug release was not affected by co-administration of a standard breakfast (Charman et al., 1993).

Cellulose particles, mechanically coated with silica or talc, are adjuvants for direct tabletting of drugs. Powdered cellulose (75.75 g.) was coated with 0.75 g. silica and used for tabletting of acetylsalicylic acid, together with Aerosil 200 and starch, as usual (Rettenmaier, 1993).

A new technique for preparation of crosslinked polyvinyl alcohol (PVA) microspheres containing various drugs has been described. An aqueous solution of PVA containing various concentrations of glutaraldehyde was dispersed as droplets in liquid parafil using a suitable sizing agent. Crosslinking of PVA droplets with glutaraldehyde was induced by an acid catalyst (HCl) which was produced by addition of small quantities of benzoyl chloride into the dispersion medium. Microspheres containing drugs such as aspirin were prepared by carrying out the crosslinking reaction in the presence of such drugs (Thanoo, 1993).

Polycarbonate microspheres loaded with aspirin were prepared by a solvent evaporation technique. High drug loading (>50%) was achieved by this process (Thanoo, 1993).

Rate and extent of bioavailability of two immediate-release acetylsalicylic acid tablet formulations were tested in 18 healthy young male volunteers after fasted single-dose administration (Blume, 1993).

A process for preparing biodegradable microparticles comprising a biodegradable polymeric binder and a biologically active agent was described. A first phase, comprising active agent and polymer, and a second phase are pumped through a static mixer into a quench liquid to form microparticles containing active agent. Preferably, a blend of at least two substantially non-toxic solvents, free of halogenated hydrocarbons, is used to dissolve or disperse the agent and dissolve the polymer. Thus, 329 g norethindrone was dissolved in 770 g Medisorb 85:15 DL-lactide-glycolide copolymer in 2.2 kg ethyl acetate and 2.2 benzyl alcohol at 65°–70° C.; then it was filtered and maintained at 65°–70° C. The aqueous phase was prepared by dissolving 150 g polyvinyl alcohol in 27.27 kg water and heating at 65°–70° C. followed by addition of 810 g benzyl alcohol and 1770 g ethyl acetate. The quench solution was prepared by dissolving 26.25 kg ethyl acetate in 750 L cold water and maintained at 2°–4° C. The organic phase was pumped through the static mixer at a flow rate of 909 mL/min, and the aqueous phase at a flow rate of 4500 mL/min into the quench solution. After one h of quench the material was passed through 90 and 25 mm screen and vacuum dried for 36 h to obtain 650 g of 30% norethindrone-loaded microparticles (Ramstack et al., 1995).

The preparation of controlled-release tablets having an internal drug containing phase and an external phase comprises a polyethylene glycol (PEG) polymer which has a weight average molecular weight of 3000–10000 was described. Acetylsalicylic acid crystals 50 kg were loaded into a coating pan and were spray-coated with a suspension containing Eudragit L30D 16.7, acetyl triethylcitrate 0.5, talc 2.5, and water 12.3 kg at 54°–60° C. for 105 min until the coated acetylsalicylic acid are formed. The coated crystals were mixed with an equal weight of PEG (av, mol. wt. 3350) at 50° C. to form a molten blend which was formed into tablets (Chen, 1995). Super et al. (1984) have studied certain acetylsalicylic acid polylactide systems.

Sustained-release preparations for bone implants comprise compressed moldings containing pharmaceuticals and polymers (and optionally artificial bone ingredients) having a coating layer containing artificial bone ingredients. Gentamicin sulfate 20, poly(lactic acid) 40, $Ca_3(PO_4)_2$-$Ca_4H(PO_4)_3$-$CaHPO_4$ mixture (A) 80 and Na chondroitin sulfate-Na succinate-water mixture (B) 22.9 mg were molded, solidified at 37° C. and humidity 50% for 24 h, sandwiched with a mixture of A and B, and solidified to give moldings which showed good sustained-release property (Ishii et al., 1995).

The present invention provides a significant advance in preparing depot forms of carboxyl-containing compounds. This relates to the surprising discovery of stable complexes formed between ester-rich polymers and such compounds according to the process described herein.

SUMMARY OF THE INVENTION

Described herein is a composition comprising a biologically active carboxylic acid-polyester complex, most preferably an aspirin-polyglycolide complex. The polyglycolide has a monomeric (repeating) glycolide unit and, in a preferred embodiment, a molecule of aspirin is associated with each monomeric unit. The term "biologically active" is used to mean having effects upon animals or plants, such as with antiinflammatory drugs, herbicides and insecticides, for example.

The preferred method of producing the polyglycolide-aspirin complex comprises mixing polyglycolide and aspirin, both in powdered form to form a mixture, melting the mixture to form a clear homogeneous liquid, and then solidifying it. This method, or obvious variants thereof apparent to those of skill in the art, will function to make numerous complexes of biologically active carboxylic acid and polyesters. In preferred embodiments the ratio of aspirin to polyglycolide monomeric unit is between about 1:1 and about 3:7.

Methods of administering the preferred polyglycolide-aspirin complex include enterally, parenterally, or topically to an organism being treated. A preferred polyester-aspirin or Ibuprofen complex use is envisioned as a suture or body-supportive (e.g., bone fragment replacement) material with a slowly released antiinflammatory agent.

More generally described herein is a composition of matter useful for the slow release of biologically active carboxyl-containing compound. The described composition is formed by preparing a molten solution of a C1–C4 hydroxy carboxylate polyester and a carboxyl-containing biologically active compound which is cooled to form a complex of the polyester and carboxyl-containing compound.

The complex can be formed using a polyester selected from the group consisting of a polyglycolide, polylactide, poly(lactide-co-glycolide) and polyhydroxybutyride and a carboxylic acid selected from the group consisting of acetylsalicylic acid, (S)-(+)4-isobutyl-α-methylphenylacetic acid (Ibuprofen), phenylacetic acid, phenoxyacetic acid, benzoic acid and salicylic acid. A preferred complex between a polyester having C1–C4 hydroxy carboxylate monomers and a carboxyl-containing biologically active compound, in a ratio of carboxylate compound to monomeric polyester unit of from about 1:10 to about 10:1.

An aspirin polyglycolide complex can be produced by preparing a molten mixture of aspirin and polyglycolide and pooling said mixture. A method for producing a complex of a C1–C4 hydroxyalkyl carboxylic acid polyester and aspirin or Ibuprofen comprises forming a molten solution of the polyester and the aspirin or Ibuprofen and cooling the solution. The hydroxyalkyl carboxylic acid can be glycolic acid, lactic acid or hydroxybutyric acid. Either one component may be melted and the other dissolved therein or the solid components first mixed and then melted. Of course mixing molten components may be done.

Also described is a method of producing a suture or bone replacement material having antiinflammatory activity comprising preparing and cooling a molten mixture of a C1–C4 hydroxyacid polyester and a carboxyl containing nonsteroidal antiinflammatory agent.

A composition of matter comprising an aspirin-polyglycolide complex prepared as described herein is considered the most preferred embodiment of the present invention. An aspirin-polyglycolide complex where the polyglycolide comprises monomeric glycolide units and about 1 molecule of aspirin is present for each monomeric unit has been prepared. One method of producing a polyglycolide-aspirin complex, includes mixing polyglycolide and aspirin to form a mixture, melting said mixture and solidifying said melted mixture. The polyglycolide has a monomeric unit and the ratio of aspirin to monomeric unit is from 1:10 to 10:1, most preferably about 1:1. The method where the polyglycolide and aspirin are in powdered form. A method of administering aspirin may comprise obtaining a polyglycolide-aspirin complex and administering said complex enterally, parenterally, or topically to an animal in need thereof. Because glycolic acid is not preferred for gastric treatment, enteric administration is less preferred.

DETAILED DESCRIPTION OF THE PREFERRED EMBODIMENTS

Figure 1:
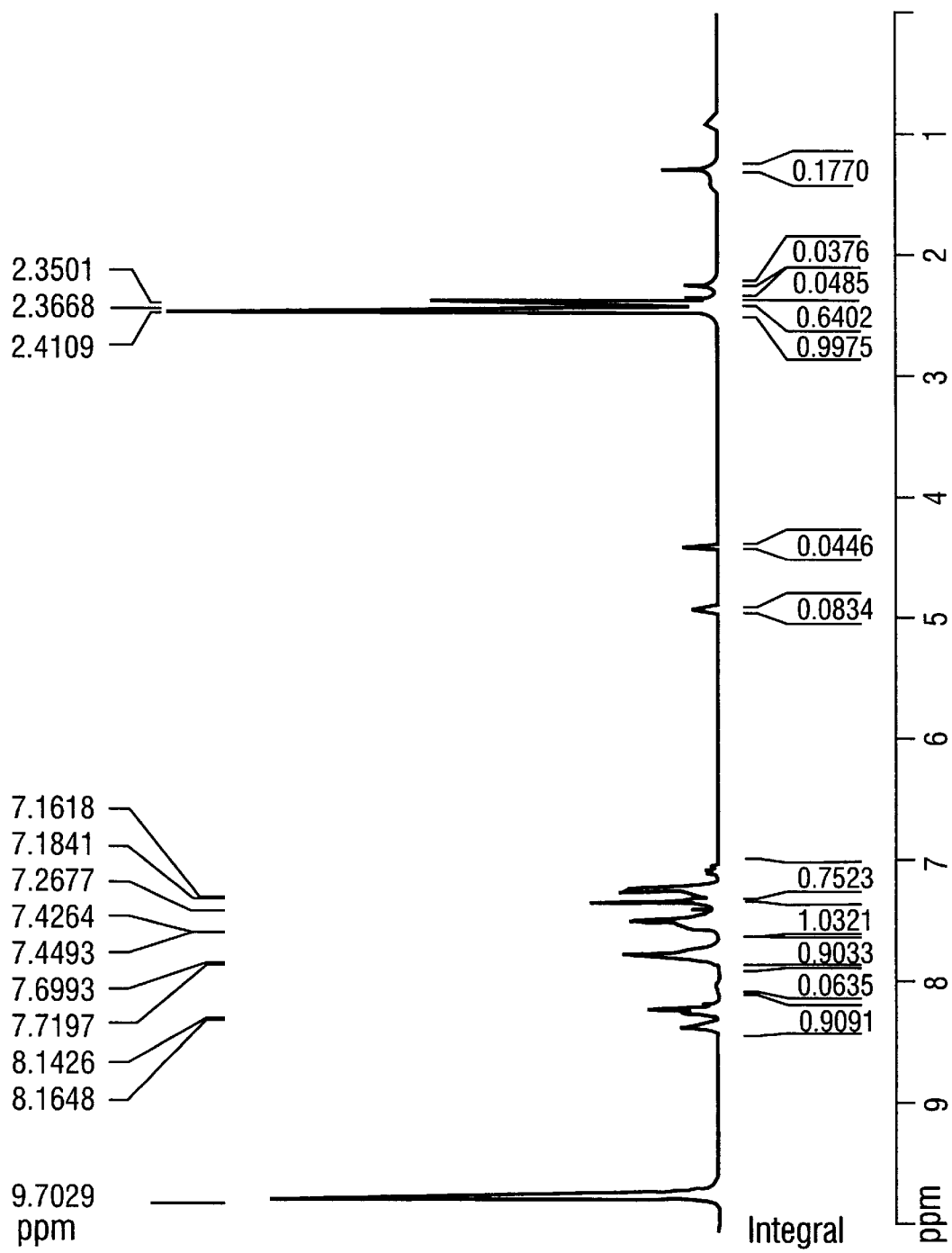
FIG. 1 shows a $^1H$ NMR spectrum of polyglycolide/aspirin composite; $CDCl_3/CF_3COOD$ solvent.

A central aspect of the present invention is the heretofore unnoticed complex formation between polyesters and carboxyl-containing compounds. Such complexes may be used to facilitate slow release of the carboxyl-containing compounds in a variety of contexts, one including a concommittance with polyester hydrolysis.

Polyesters specifically tested include polyglycolide, polylactide and poly (DL-lactide-co-polyglycolide). Persons having ordinary skill in the art understand that other polyesters, including those of other alpha-hydroxy carboxylic acids such as, e.g., alpha hydroxybutyrate and the like will form analogous complexes.

Carboxyl-containing compounds specifically found to bind polyesters include acetylsalicylic acid (aspirin); (s)-(+)-4-isobutyl-α-methylphenylacetic acid (Ibuprofen), benzoic acid, salicylic acid, phenoxyacetic acid and phenylacetic acid.

The present invention includes synthesis of a polyglycolide and aspirin composite in which aspirin molecules are bound to the repeating units of polyglycolide. Experimental evidence shows that at least one aspirin molecule may be bonded to each monomeric unit of polyglycolide. This binding, when equal amounts of aspirin and polyglycolide monomeric units are used, is about 1:1. A 3:7 ratio has also been prepared. Of course, if less aspirin is used, the ratio may be decreased at will. A 1:10 ratio or even lower may be suitable for some purposes.

The polyglycolide/aspirin composite (PAC) releases aspirin molecules as polyglycolide is degraded. The aspirin molecules would be made available to be physiologically effective. This physiological effect will involve reducing or eliminating inflammation and/or pain. PAC may be ingested or inserted close to the site of the pain origin in order to be more effective as well as to extend the effect over a longer period of time.

Substitutes for polyglycolide such as polylactide or other polyesters may be used: Polymers rich in ester groups but not polyesters, e.g., polymethylmethacrylate should bind aspirin and the like. However, because they are not readily hydrolysable or biodegradable, such polymer composites are viewed as of more limited use. Likewise, in place of aspirin, other substances, particularly those bearing free carboxyl groups may be used. For example, phenoxyacetic acid, salicylic acid an benzoic acid all have been found to interact with polyglycolide. Simple homologs and derivatives of aspirin, such as those having halogen, methyl, methoxy, nitro and like substituents on the phenyl or acetyl will also form analogous polyester complexes. The preparation of these or other composites is analogous to that of PAC and the formation similarly monitored.

EXAMPLE 1

Synthesis of Polyglycolide/Aspirin Composite

Polyglycolide, prepared as previously reported (Ginde et al., Pinkus et al.), and acetylsalicylic acid (99+%), both in finely powdered form, were mixed intimately in the ratio of 58.0 g. to 180 g., respectively corresponding to the repeating unit molar amount of polyglycolide (—$CH_2COO$—) and molecular weight of acetylsalicylic acid ($C_9H_8O_4$). The mixture was heated in a sand or oil bath until it melted to a clear liquid. The clear liquid was then allowed to solidify. Measurements were made on this material.

Figure 2:
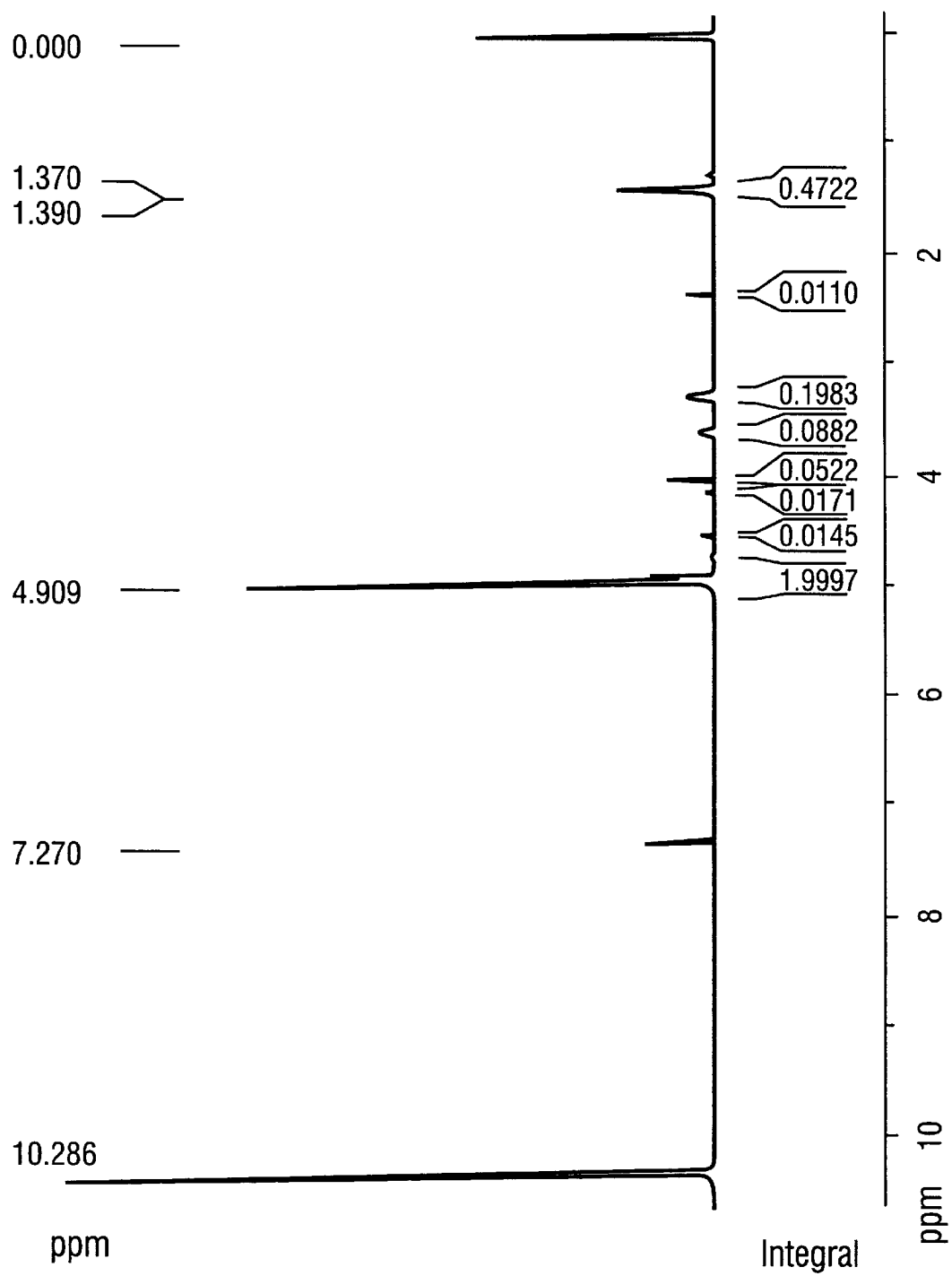
FIG. 2 shows $^1H$ NMR spectrum of polyglycolide; same solvent as with FIG. 1.
Figure 3:
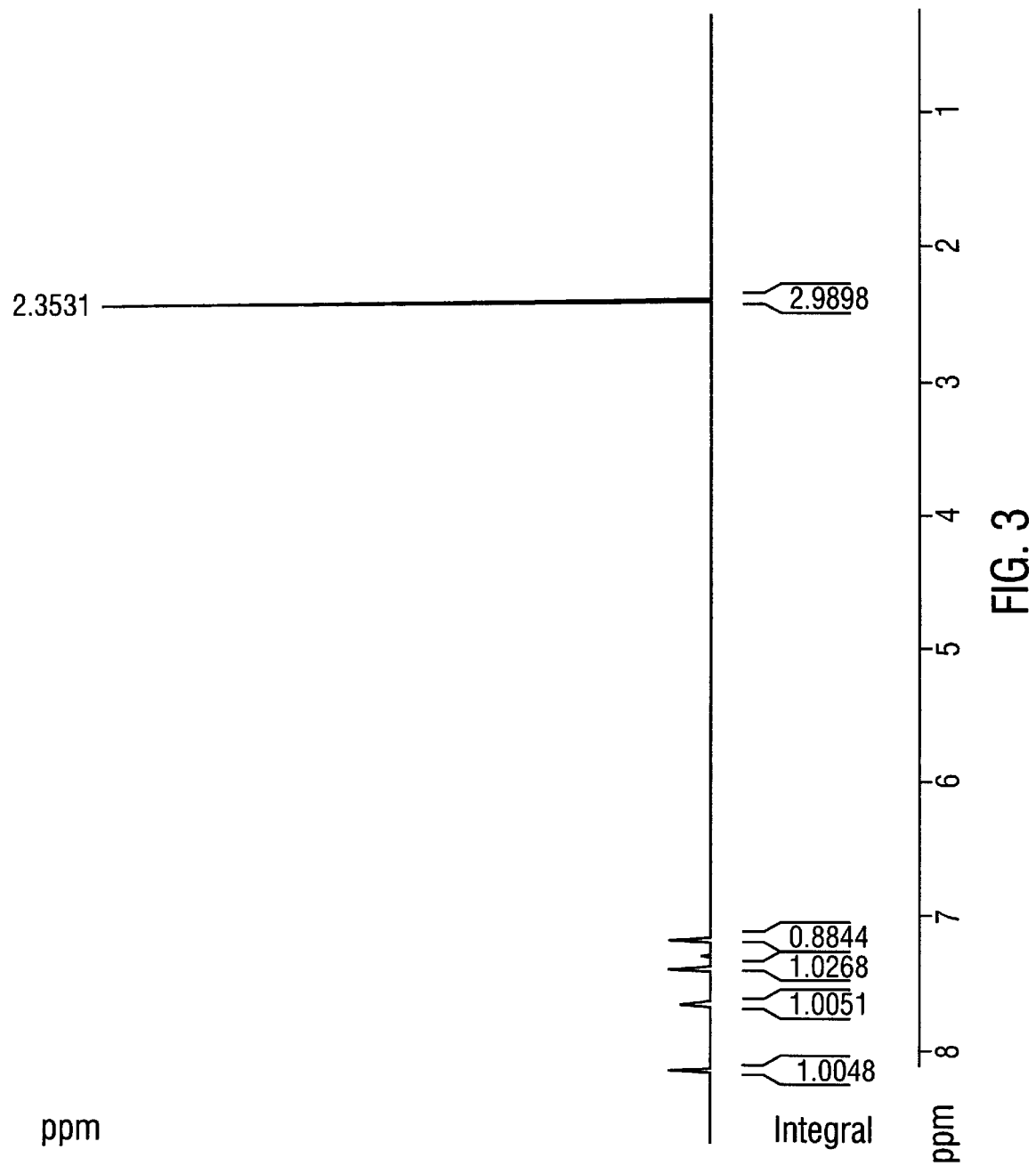
FIG. 3 shows $^1H$ NMR spectrum of aspirin; 99+%; $CDCl_3$ solvent.
Figure 4:
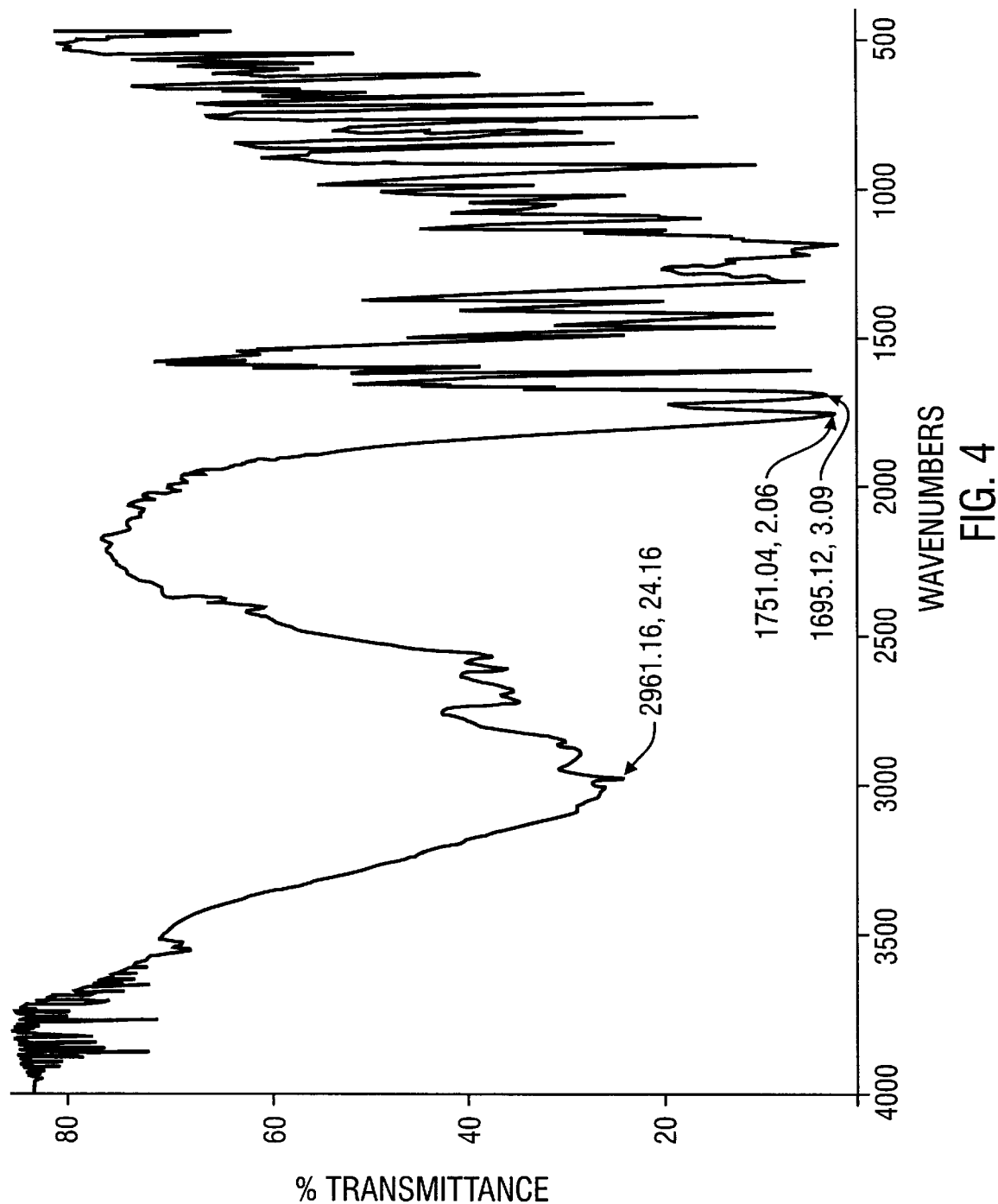
FIG. 4 shows FT-IR spectrum of polyglycolide/aspirin composite; KBr disc.
Figure 5:
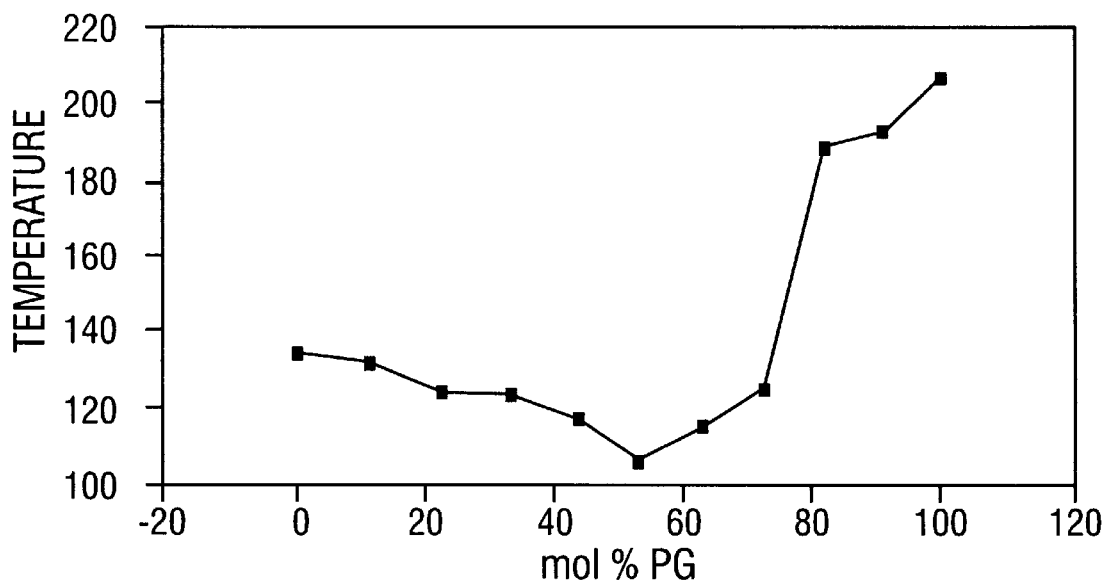
FIG. 5 shows a $T_m$/mole composition plot for polyglycolide/aspirin composite.

The $^1H$ nuclear magnetic resonance (NMR) spectrum PAC (FIG. 1) showed that the peak for the $CH_2$ protons of polyglycolide originally at δ 4.91 (FIG. 2) was missing except for a small residual and had shifted far upfield to about 2.36 (a shift of about 2.6 p.p.m.) next to the acetyl $CH_3$ peak of acetylsalicylic acid at about 2.41 δ. This showed that the $CH_2$ protons of the polyglycolide were shielded by the aspirin molecules. A likely interpretation is that an aspirin molecule is anchored to each carbonyl oxygen of polyglycolide by hydrogen bonding with the carboxyl hydrogen so that the benzene ring π-electron cloud is above the $CH_2$ group, resulting in shielding and requiring a higher magnetic field to bring these protons into resonance. A $^1H$ NMR spectrum of acetylsalicylic acid (FIG. 3) shows that the acetyl ($CH_3C$=O) and benzene ring proton signals (at 2.35 and about 7–8 δ, respectively) do not change position much even considering that the latter spectrum is in $CDCl_3$ whereas the former spectra are in a $CDCl_3/CF_3COOD$ solution because of the insolubility of polyglycolide in most solvents (Hariharan et al.). An infrared spectrum (FIG. 4) shows the two strong carbonyl stretching peaks expected for the acetyl ester group in aspirin and the ester group in polyglycolide at 1695 and 1751 $cm^{-1}$ and a broad band >3000 $cm^{-1}$ indicating strong hydrogen bonding. A melting temperature (*$T_m$)/composition plot (FIG. 5) also furnishes evidence for the 1:1 ratio between each aspirin molecule and each glycolide repeating unit [—($CH_2COO$)—]. It can be noted that the minimum $T_a$ is close to the 50% mole ratio indicating also a 1:1 correspondence of molecules of aspirin to the polyglycolide repeating unit.

EXAMPLE 2

Preparation of Polyglycolide-Aspirin Combination

As an example of the various possible ratios of polyglycolide-aspirin combinations, a 30:70 mole ratio of polyglycolide monomer:aspirin is described. Polyglycolide and aspirin were finely powdered and weighed. Polyglycolide (0.116 g, 2.00×10–3 mole) and aspirin (0.84 g, 4.70×10–3 mole) in a flask under an argon atmosphere were heated in an oil bath to a temperature at which the lower-melting aspirin melted and dissolved the polyglycolide. On cooling, the melt solidified. The solid was powdered.

EXAMPLE 3

Polyglycolide Hydrolysis Procedure I

Hydrolysis was carried out with samples of the 30:70 polyglycolide monomer:aspirin mole ratio and polyglycolide alone for comparison as a standard.

Polyglycolide hydrolyses

Samples of polyglycolide approximately 0.3 g (Table 1) were weighed and transferred into clean centrifuge tubes. Distilled water (15 mL) was added to each tube and the mixtures were shaken in a water bath/shaker at 22° C. for various periods of time when selected samples were removed and centrifuged for about 5 minutes. Aliquots of the clear supernatant solution were taken for analysis.

Titration

Aliquots were titrated with 0.0923N NaOH solution, using bromphenol blue indicator, for the glycolic acid hydrolysis product. Results are in Table 1. Since varying amounts of sample and aliquots of hydrolysis solution were taken, the volumes of NaOH used were normalized to 1.0 g of sample and 1.0 mL of aliquot by dividing by the weights of samples and volumes of aliquots to give a corrected volume of NaOH (Table 1).

TABLE 1

Hydroloysis of polyglycolide: water, 22° C. Each sample titrated with 0.0923 N NaOH

| | Time (hr) | W (g) Polygly | V aliq. (mL) | V NaOH (mL) | V NaOH (mL)* |
|---|---|---|---|---|---|
| 1 | 1 | 0.302 | 7.5 | 0.25 | 0.11 |
| 2 | 3 | 0.302 | 6.8 | 0.27 | 0.13 |
| 3 | 24 | 0.303 | 7.5 | 0.36 | 0.16 |
| 4 | 48 | 0.307 | 7.5 | 0.39 | 0.17 |
| 5 | 72 | 0.307 | 6.2 | 0.39 | 0.21 |
| 6 | 96 | 0.327 | 7.0 | 0.44 | 0.19 |
| 7 | 120 | 0.327 | 7.0 | 0.52 | 0.23 |

V aliq. (mL) = volume of aqueous hydrolysis medium taken for titration after centrifuging.
V NaOH (mL) = volume of NaOH solution used with bromphenol blue indicator endpoint.
V NaOH (mL)* - volume of NaOH solution normalized for varying weights of polyglycolide sample and varying volumes of hydrolysis solution aliquot.

EXAMPLE 4

Polyglycolide-aspirin combination hydrolyses

The hydrolyses were carried out by the same procedure as for polyglycolide. Results are in Table 2.

TABLE 2

Hydrolysis of polyglycolide:aspirin (30:70 mole ratios); water, 22° C. Each sample titrated with 0.0923 N NaOH.

| | Time (hr) | W (g) PolyAsp | V Aliquot (mL) | V NaOH (mL) | V NaOH (mL)* |
|---|---|---|---|---|---|
| 1 | 1 | 0.3074 | 7.5 | 0.12 | 0.05 |
| 2 | 3 | 0.3074 | 7.2 | 0.30 | 0.14 |
| 3 | 24 | 0.3053 | 7.0 | 0.26 | 0.12 |
| 4 | 48 | 0.3033 | 7.5 | 0.36 | 0.16 |
| 5 | 72 | 0.3053 | 7.0 | 0.67 | 0.31 |
| 6 | 96 | 0.3114 | 7.0 | 0.69 | 0.32 |
| 7 | 120 | 0.3114 | 7.0 | 0.72 | 0.33 |

V aliq. (mL) = volume of aqueous hydrolysis medium taken for titration after centrifuging.
V NaOH (mL) = volume of NaOH solution used with bromphenol blue indicator endpoint.
V NaOH (mL)* -= volume of NaOH solution normalized for varying weights of polyglycolide-aspirin sample and varying volumes of aliquot of hydrolysis solution.

Figure 6:
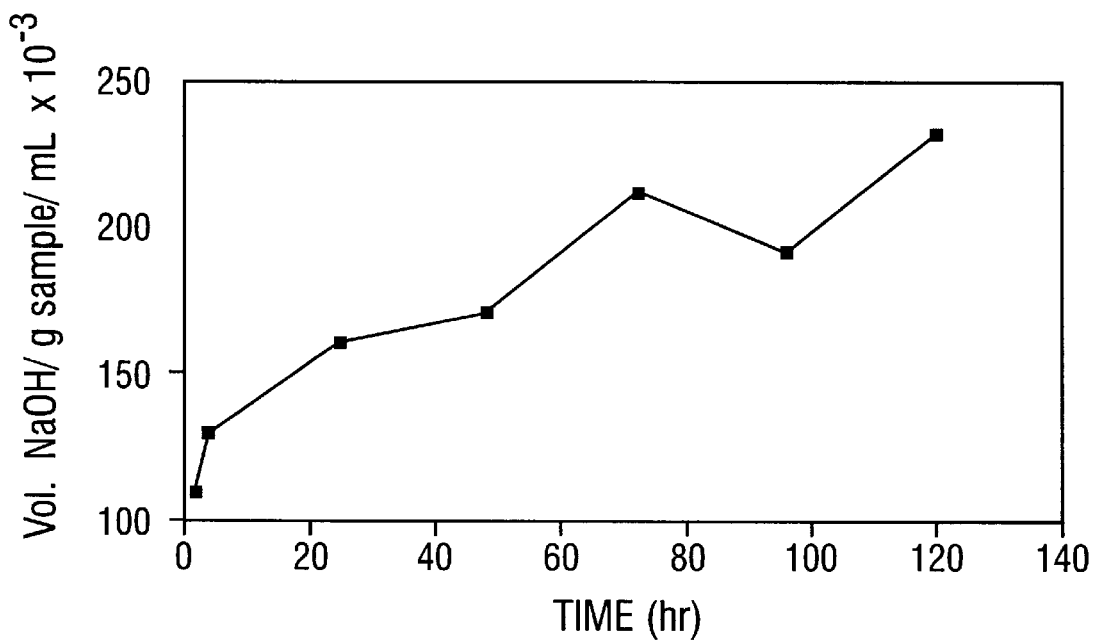
FIG. 6 shows hydrolysis of polyglycolide: water, 22° C. Each sample titrated with 0.0923N NaOH.

For polyglycolide hydrolysis, the corrected volume of NaOH used in the titration is plotted against time of hydrolysis in FIG. 6. After an initial release of acid, hydrolysis proceeds at a moderate rate with time.

Figure 7:
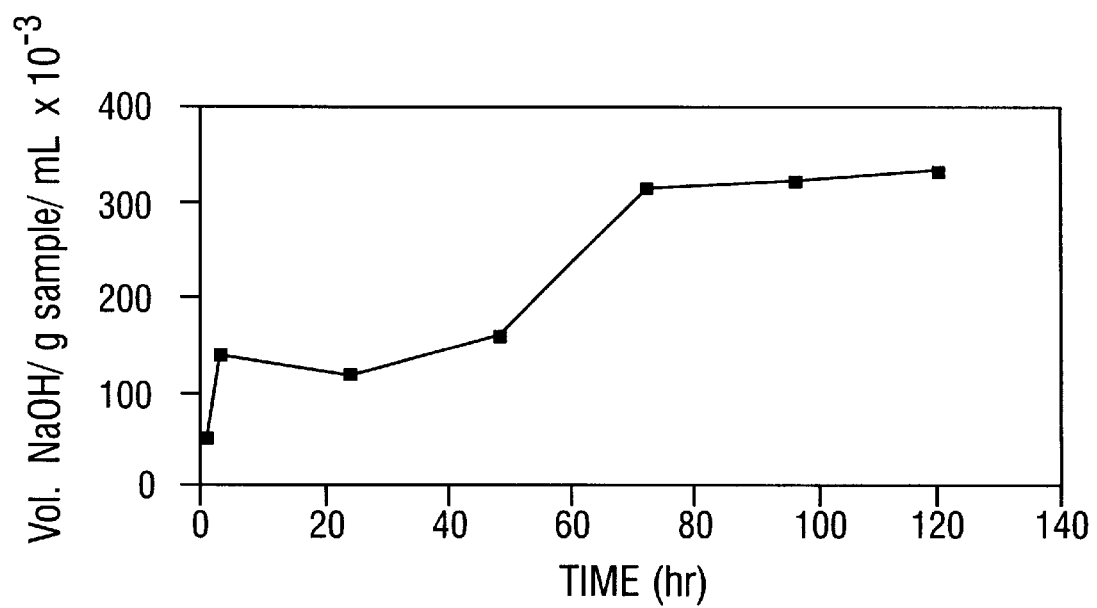
FIG. 7 shows hydrolysis of polyglycolide:aspirin (30:70 mole %): water, 22° C. Each sample titrated with 0.0923N NaOH.

For hydrolysis of the polyglycolide/aspirin combination, results are plotted in FIG. 7. After an initial fast acid release, further release of acid product levels off and then increases for about 72 hours, after which release of acid product increases slowly with time to 120 hours.

For a 90:10 (asp:Polygly) combination (Tm=123°–125° C.): For a 0.3004 g. sample shaken for 3 hours, a 9.5 mL aliquot required 1.1 mL of 0.0923N NaOH. When this volume of NaOH is normalized to account for the weight of sample and volume of aliquot, the corrected volume of NaOH is 0.39 mL per g. sample per mL. aliquot. This can be compared with the normalized volume of 0.12 mL of NaOH required for the corresponding 3 hour hydrolysis of the 70:30 mole ratio combination, over a three-fold increase in the release rate on this basis of comparison. This shows that the rate of release of aspirin can be controlled by the mole ratio of the aspirin:polyglycolide combination.

For the 95:5 (asp:Polygly) combination (Tm-123°–125° C.): For a 0.3009 g. sample shaken for 3 hours, a 9.5 mL aliquot required 1.31 mL of 0.0923N NaOH. When this volume of NaOH is normalized to account for the weight of sample and volume of aliquot, the corrected volume of NaOH is 0.46 mL per g. sample per mL. aliquot, an increase over the 90:10 combination. This is further evidence that the rate of release of aspirin can be controlled by the mole ratio of the aspirin:polyglycolide combination.

It is evident that when aspirin is combined in a homogeneous manner with polyglycolide, release is substantially modified since although aspirin readily dissolves in water to the extent of 1 gram/300 mL at 25° C., for the 30:70 mole ratio polyglycolide:aspirin combination (where aspirin is present to the extent of 88% by weight), only a small amount of aspirin and combined aspirin-glycolic acid is released even after 5 days of shaking a powdered sample with water. The rate of release can be increased by increasing the % of aspirin in the combination.

Using aspirin alone (sample of 0.3019 g comparable to amounts used with polyglycolide combinations), after shaking 3 hours with 15 mL of water, an aliquot of the solution (14 mL) required 2.6 mL of 0.0923N NaOH. On calculation, this corresponds approximately to the solubility of aspirin in water as expected. This contrasts markedly with the slow release from the 30:70 mole % combination (containing ~88% aspirin).

EXAMPLE 5

Hydrolysis Procedure II

For Polyglycolide:

The trial runs involved only 0.1 g of polyglycolide in 15 mL distilled water. The hydrolysis for the recorded trials is explained here. The hydrolysis was carried out in a water bath/shaker at room temperature (22° C.). Samples weighing approximately 0.30 g were weighed out into clean centrifuge tubes (1 mL). Each tube was then filled with 15 mL of distilled water. Four tubes were prepared in this manner. They were labeled pg1 (48 and 72 hours), pg2 (96 and 120 hours), pg3 (24 hours), pg4 (1 and 3 hours). All the tubes were placed in the bath for their allotted times. From each tube, after centrifuging for about 5 minutes, an aliquot of about 7.0–7.5 mL in volume was taken. The aliquots were representative of the time that the sample was allowed to hydrolyze for. For example, pg1 was removed after 48 hours and a 7. mL aliquot was removed and then titrated. Pg1 was then put back into the bath for its remaining allotted time— 72 hours. Then a second aliquot was removed and then titrated. The titrations involved the use of a 1.0 mL syringe to dispense the 0.0923N NaOH basic solution into the aliquots. Since glycolic acid was the expected product of hydrolysis, an indicator was chosen to match its pH range to the pKa of glycolic acid (3.83). Bromphenol blue was chosen because its pH range is 3.0–4.6. About three drops of indicator were added to the aliquots. The aliquots were titrated from a yellow color to the faintest tinge of purple.
For combination:

The procedure for the hydrolysis of the combination was essentially the same as for the polyglycolide. The amount of samples were the same as well as the amounts of water added and aliquots removed. Time intervals were the same.

Figure 8:
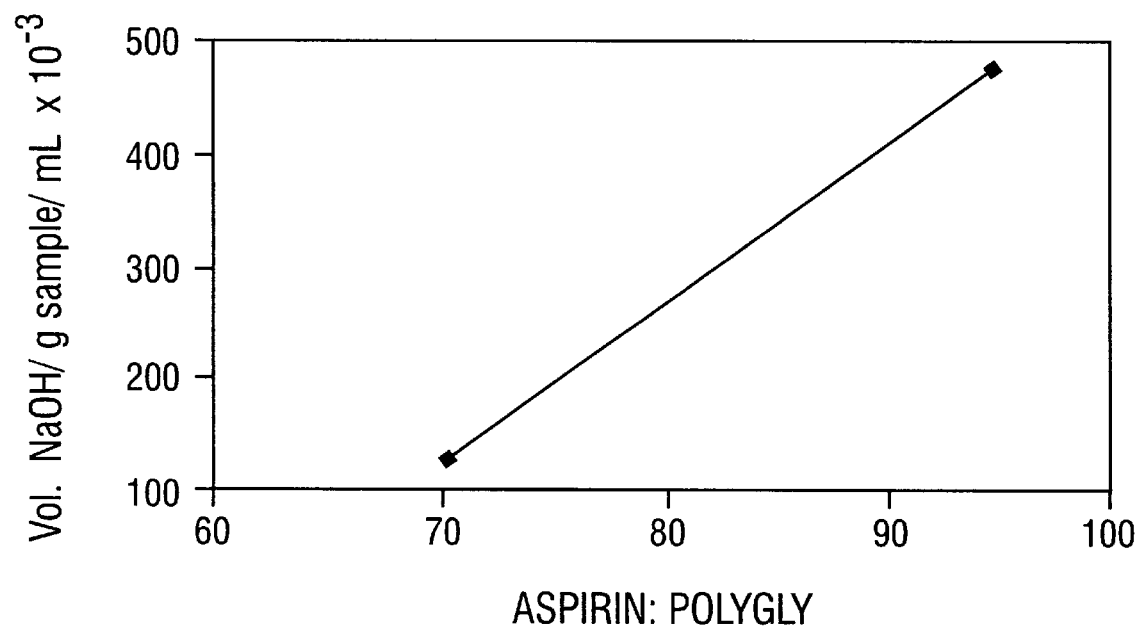
FIG. 8 shows hydrolysis of polyglycolide:aspirin (mole %): water, 22° C. Each sample titrated with 0.0923N NaOH.

FIG. 8 and Table 3 show a summary of the Poly:Asp hydrolysis data. Note the nice straight line for the plot of mole ratio vs. normalized (corrected) volume of NaOH per g of sample per mL of aliquot titrated. The rate of release can be determined from the polygly:asp mole ratio. (This is for a three hour hydrolysis. Further studies will be carried out for longer times and with other hydrolysis mixtures.)

TABLE 3

Hydrolysis of polyglycolide:aspirin (mole ratios); water, 22° C. Each sample titrated with 0.0923 N NaOH.

| | Aspirin:Polygl | V(Na)H)/g/mL |
|---|---|---|
| 1 | 95 | 0.46 |
| 2 | 90 | 0.39 |
| 3 | 70 | 0.12 |

V(NaOH)/g/mL (mL) = volume of NaOH solution normalized for varying weights of polyglycolide-aspirin sample and varying volumes of aliquot of hydrolysis solution.

EXAMPLE 6

Aspirin/Polylactide Combinations

Polylactide and copolymers of polylactide and polyglycolide are also used as biodegradable materials. In view of the success with the homogeneous dispersal of aspirin in polyglycolide, the dispersal of aspirin in polylactide and polylactide/polyglycolide copolymers was investigated. Although a few references have appeared for the use of polylactide and its copolymers with polyglycolide for controlled release, none of these have incorporated aspirin according to the processes described herein.

EXAMPLE 7

Preparation of Aspirin/Polylactide Combination

The reagents were commercially purchased compounds. The polylactide was about 96% L-isomer. $T_m$ was determined to be about 138° C. The amount of polylactide used was based on the repeating unit (—CHCH$_3$COO—) per molecule of aspirin. The aspirin (acetylsalicylic acid or 2-acetoxybenzoic acid) $T_m$ was 138°–140° C. The two components were mixed in powdered form in a flask protected by a drying tube in the amounts, 0.147 g (0.00204 mol) polylactide and 0.353 g (0.00202 mol) aspirin and heated in an oil bath until the mixture just melted to a clear homogeneous liquid, at which point the flask was allowed to cool to room temperature. The temperature was kept as low as possible and reagents were not heated any longer than necessary to liquefy them in order to avoid any possible decomposition. The solid product was powdered and $T_m$ determined to be 129°–132° C.

EXAMPLE 8

Preparation of Aspirin/Poly[(DL-lactide-co-glycolide)] (65:35) Combination

The poly[DL-lactide-co-glycolide)] (65:35) (I) was a commercially purchased material. The mole ratio was based on the repeating unit, (—CHCH$_3$COO—)$_{65}$—(—CH$_2$COO—)$_{35}$ assuming that each repeating unit hydrogen-bonds to two aspirin molecules or a ratio of aspirin:I of (180×2):67.1 (in grams). The procedure was the same as that described above for polylactide. The two components were mixed in the ratio of aspirin (0.608 g, 0.00338 mol) to I(0.138 g, 0.00206 mol) or 0.00338×2 mol aspirin to 0.00206 mol of I or 3.28 aspirin: 1.00 mol of I. This mixture became a clear liquid with the oil bath at about 138° C. Tm of the solid obtained after cooling was 128°–131° C.

Other polylactide/polyglycolide copolymers are commercially available, such as Poly(DL-lactide-co-glycolide) (85:15), (75:25), and (50:50). It is evident that similar combinations of these and aspirin may be prepared.

EXAMPLE 9

Preparation of Polyglycolide/Ibuprofen Combination

Based on the successful combination of aspirin and polyglycolide, the application of the method used was applied to ibuprofen as an example of another commonly used medicinal containing a carboxyl group. This experiment is described.

Two different brands of commercially purchased ibuprofen [(S)-(+)-4-isobutyl-α-methylphenylacetic acid] were used, m.p. 51°–53° C. Polyglycolide was synthesized by a published procedure (Pinkus, A. G. et al. 1984), m.p. 212°–214° C.

The reagents in powdered form were mixed in the proportions, polyglycolide (0.116 g, 0.002 mol) to ibuprofen (0.383 g, 0.00186 mol) (2nd sample: 0.381 g, 0.00185 mol) and heated in a moisture-protected flask by the procedure described above for polylactide. $T_m$ of the solid products obtained were 186°–189° C.

EXAMPLE 10

Naproxen

Another medicinal that is commonly used for relief of pain and contains a carboxyl group is "naproxen" (6-methoxynaphthyl-2-propanoic acid). The melting point for the commercially obtained material was 157°–158° C. However, when the same procedure was used with a mixture consisting of naproxen and polyglycolide, the mixture turned dark, an apparent decomposition.

EXAMPLE 11

Preparations of Other Combinations of Polyglycolide and Carboxylic Acids

These were prepared by the same procedures as described above to demonstrate the generality of the method. Among the carboxylic acids used were: benzoic acid, salicylic acid, and phenylacetic acid. It is thought that hydrogen-bonding of the carboxylate group of the carboxylic acid to the oxygens of the polyglycolide facilitates the combination. In the cases where the molar ratio of the acid to the repeating units of polyglycolide exceeds a 1:1 ratio for aspirin, additional hydrogen-bonding of the carboxylate group to the oxygens of the ortho-acetoxy group of aspirin can also take place.

The following references are incorporated by reference herein for the reasons cited above.

Anon. (USA) Sustained Release Compositions. Res. Discl. 1985, 259, 567–570. (Chem. Abstr., 1986, 104, 116017)

Asch, R. H.; Rojas, F. J.; Tice, T. R.; Schally, A. V. Studies of a Controlled-release Microcapsule Formulation of an LH-RH Agonist (D-Tip-6-LH-RH) in the Rhesus Monkey Menstrual Cycle. Int. J. Fertil. 1985, 30, 19–26. (Chem. Abstr., 1986, 104, 116019)

Bechgaard, H.; Gravensev, P. O.; Petersen, A. M. Rate of Drug Release from Intact and Subdivided Tablets, Arch. Pharm. Chemi, Sci. Ed. 1977, 5, 21–22. (Chem. Abstr., 1977, 86, 195155)

Blume, H.; Scheidel, B.; Siewert, M.; Wendt, G. Bioavailability of Acetylsaltcylic Acid Based Analgesics. 6. Bioavailability of Two Immediate-Release ASA Tablet Formulations. PZ Wiss. 1993, 6, 59–64. (Chem. Abstr., 1993, 119, 125048)

Blume, H.; U. Gundert-Remy; Möller, H., eds. Controlled/Modified Release Products. Recommendation in Support of EC-Guidelines, Stuttgart, Ger.: Wissenschaftliche Verlagsgesellschaft mbH, 1991.

Brantmark, B.; Waahlin-Boll, E.; Melander, A. Bioavailability of Acetylsalicylic Acid and Salicylic Acid from Rapid and Slow-release Formulations, and in Combination with Dipyridamol. Eur. J. Clin. Pharmacol. 1982, 22, 309–314. (Chem. Abstr., 1982, 97, 98248)

Casadio, S.; Sclavi, E.; Perego, R. Acetylsalicylic Acid-containing Drugs with Sustained Release, Ger. Offen. 2,149,699, Apr. 13, 1972, Brit. Appl. 48,167/70, Oct. 9, 1970. (Chem. Abstr., 1972, 77, 1972)

Chapman, D. G.; Shenoy, K. G.; Campbell, J. A. Sustained Release of Drugs in Certain Drug-resin Complexes as Judged by Urinary Excretion Rates, Can. Med. Assoc. J. 1959, 81, 470–476. (Chem. Abstr., 1960, 54, 4904.

Charles, H. Sustained-release Aspirin. PCT Int. Appl. WO 84 00,004, Jan. 5, 1984, U.S. application Ser. No. 388, 183, Jun. 14, 1982. (Chem. Abstr., 1984, 100, 126906)

Charman, W. N.; Charman, S. A.; Monkhouse, D. C.; Frisbee, S. E.; Lockhart, E. A.; Weisman, S.; Fitzgerald, G. A. Biopharmaceutical Characterization of a Low-dose (75 mg) Controlled-release Aspirin Formulation, Br. J. Clin. Pharmacol., 1993, 36, 470–473. (Chem. Abstr., 1994, 120, 14804)

Chem. Abstr., 199?,

Chen, C. M. Controlled-release Tablets Comprising Coated Cores and PEG Coatings. U.S. Pat. No. 5,458, Oct. 17, 1995, Appl. 205,005, Mar. 2, 1994. (Chem. Abstr., 1995, 123, 350294)

Chick, J. A. Programmed-release Compositions Containing Acetylsalicylic Acid and Dihydroergotamine. Fr. Demande 2,539,989 Aug. 3, 1984, Appl. 83/1,577, Jan. 28, 1983. (Chem. Abstr., 1984, 101, 235613)

Chick, J. A. Programmed-release Pharmaceuticals Containing Acetylsalicylic Acid. Eur. Pat. Appl. EP 115,986, Aug. 15, 1984, Fr. Appl. 83/1,576, Jan. 28, 1983. (Chem. Abstr., 1984, 101, 157704)

Choudhury, S.; Mitra, A. K. Kinetics of Aspirin Hydrolysis and Stabilization in the Presence of 2-Hydroxypropyl b-Cyclodextrin, Pharm. Res., 1993, 10, 156–159.

Chowdary, K. P. R.; Rao, G. N. Studies on a New Technique of Microencapsulation: Part V. Microencapsulation of Aspirin by Ethyl Cellulose. Indian Drugs, 1985, 22, 479–481. (Chem. Abstr., 1985, 103, 183511)

Deasy, P. B.; Murtaugh, P. W. Controlled Release Antiplatelet Product Containing Dipyridamole and Aspirin, Proc. Int. Symp. Controlled Release Bioact. Mater., 20th, 1993, 286–287. Ed. by Roseman, T. J. et al., Controlled Release Soc.: Deerfield, Ill. (Chem. Abstr., 1993, 119, 233957)

Dong. C.; Rogers, J. A. Acacia-gelatin Microencapsulated Liposomes: Preparation, Stability, and Release of Acetylsalicylic Acid, Pharm. Res., 1993, 10, 141–146. (Chem Abstr., 1993, 118, 87535)

Dunn, J. M. Sustained-release Aspirin Formulation. U.S. U.S. Pat. No. 4,520,009, May 28, 1985, Appl. 555,700, Nov. 28, 1983. (Chem. Abstr., 1985, 103, 42671)

Dunn, J. M.; Lampard, J. F. Controlled Release Formulations of Orally-active Medicaments. U.S. U.S. Pat. No. 4,308,251, Dec. 29, 1981, U.S. application Ser. No. 111,430, Jan. 11, 1980; Cont.-in-part of U.S. Ser. No. 111,430, abandoned. (Chem. Abstr., 1982, 96, 74636)

Dunn, J. M.; Lampard, J. F. Pharmaceutical Composition with a Prolonged Effect. Fr. Demande 2,473,308, Jul. 17, 1981, U.S. application Ser. No. 111,430, Jan. 11, 1980. (Chem. Abstr., 1981, 95, 225675)

Dunn. J. M. Constant Order Release Aspirin Composition and Method of Treating Arthritis. U.S. U.S. Pat. No. 4,375,468, Mar. 1, 1983, U.S. application Ser. No. 282, 544, Jul. 13, 1981; Cont. of U.S. application Ser. No. 282,544, abandoned. (Chem. Abstr., 1983, 98, 185604)

Fong, J. W. Microspheres. U.S. Pat. No. 4,166,899, Sep. 4, 1979, application Ser. No. 827,710. (Chem. Abstr., 1980. 92, 28581)

Froemming, K. H.; Topaloglu, Y. Influence of Ethanol on the In Vitro and In Vivo Drug Release from Some Sustained Release Tablets. Arzneim.-Forsch. 1975, 25, 1958–1964. (Chem. Abstr., 1976, 84, 99089)

Fujimoto, M. Aspirin-dextrin Inclusion Compounds. Jpn. Kokai Tokkyo Koho 78,124,607, Oct. 31, 1978, application Ser. No. 77/39,791, Apr. 6, 1977. (Chem. Abstr., 1979, 90, 76581)

Gaudy, D.; Michel, J. P.; Maillols, H.; Rolim, P.; Acquier, R.; Delonca, H. Controlled-release Acetylsalicylic Acid Hydrophilic Matrix Tablets, Congr. Int. Technol. Pharm. 6th 1992, 3, 365–372. (Chem. Abstr., 1993, 119, 55997)

Gilding et al., *Polymer,* 1979, 20, 1459–1460.

Ginde et al., *Appl. Polym. Sci.,* 1987, 33, 2411–2429.

Guy, M. G.; Powers, R. G. Timed-release Aspirin U.S. Pat. No. 4,025,613, May 24, 1977, Appl. No. 163,739. Jul. 19, 1971. (Chem. Abstr., 1977, 87, 44251)

Habib, F. S.; El-Sourady, H. A.; Mohamed, S. E. Effect of Certain Additives on the Diffusion Characteristics of Aspirin, Salicylamide, and Phenacetin Through a Cellophane Membrane. II. Effect of Aliphatic Acids and Polyethylene Glycol. Bull. Pharm. Sci. Assiut Univ. 1984, 7, 398–417. (Chem. Abstr. 1986, 104, 174526)

Hariharan et al., *Polym. Bull.,* 1993, 30, 91–95.

Hosoi, F.; Saito, K.; Makauchi, K.; Koishi, M. Use of Porous Particles for Preparation of Capsules Containing Aspirin and Drug Release Properties. Kobunshi Ronbunshu, 1985, 42, 415–422. (Chem. Abstr., 1985, 103, 166045)

Hutchinson, F. G.; Furr, B.J.A., *Biochem. Soc. Trans.,* 1985, 13, 520–523. (*Chem. Abstr.,* 1985, 103, 42567)

Ikada, Y.; Gen, J. Sustained-release Pharmaceuticals Containing Lactic Acid Polymers. Jpn. Kokai Tokkyo Koho JP 60,181,029 [85,181,029], Sep. 14, 1985, application Ser. No. 84/36,127, Feb. 29, 1984. (Chem. Abstr., 1986, 104, 39744)

Ishii, Y.; Yamakawa, I.; Watanabe, S. Sustained-release Preparations for Bone Implants. Jpn. Kokai Tokkyo Koho JP 7,157,439, Jun. 20, 1995, application Ser. No. 93/339, 812, Dec. 7, 1993. (Chem. Abstr., 1995, 123, 179584)

Karahalios, W. J.; Sawyer, W. T.; Rittase, R. A.; Maynard, S. A. Comparative Bioavailability of Sustained-release and Uncoated Aspirin Tablets. Am. Hosp. Pharm. 1981, 38, 1754–1756. (Chem. Abstr., 1982, 96, 11606)

Kawashima, Y.; Li, S. Y.; Kasai, A.; Handa, T.; Takenaka, H. Preparation of a Prolonged-release Tablet of Aspirin with Chitosan. Chem. Pharm. Bull., 1985, 33, 2107–2113. (Chem. Abstr., 1985, 103, 42571)

Khan, M. H.; Alam, M. The In Vitro Study of Sustained Release Aspirin Tablet with Polyethylene Resin as Insoluble Matrix. Pak. J. Sci. Ind. Res. 1980, 23, 283–286. (Chem. Abstr., 1981, 95, 49299)

Kitajima et al. (Ger. Offen. 2,001,726, Jul. 23, 1970, Japan) *Chem. Abstr.,* 1979, 73, 78221.

Kitajima, M.; Kondo, A.; Yamaguchi, T.; Muroya, N. Encapsulation with Polymeric Materials, Ger. Offen. 2,001,726, Jul. 23, 1970, Japan. Appl. Jan. 16–17, 1969. (Chem. Abstr., 1970, 73, 78221)

Kydonieus, A., ed. Treatise on Controlled Drug Delivery, New York: Marcel Dekker, 1991.

Li, F.; Gu, Z.; Li, G.; Feng, X. Copolymer of 1-(Acetylsalicyloyloxy)ethyl Methacrylate and Its Hydrolysis. Gaofenzi Tongxun, 1984, (5), 393–396. (Chem. Abstr., 1985, 102, 190971)

Li, S. P.; Pendharkar, C. M.; Mehta, G. N.; Karth, M. G.; Feld, K. M. Sucralfate as a Bioadshesive Gastric Intestinal Retention System: Preliminary Evaluation, Drug. Dev. Ind. Pharm., 1993, 19, 2519–2537. (Chem. Abstr., 1994, 120, 14821)

Linhardt. R. J. Biodegradable Polymers for Controlled Release of Drugs. Chap. 2, p 82 in Rosoff, M. Controlled Release of Drugs (see ref. below).

Lobeck, F.; Spigiel, R. W. Bioavailability of Sustained-release Aspirin Preparations. Clin. Pharm. 1986, 5, 236–238. (Chem. Abstr., 1986, 104, 174521)

Molloy, T. P.; Lee, D.; Chopra, S. K. Method for Production of Solid Pharmaceutical Dosage Forms, PTC Int. Appl. WO 92 11,845 Jul. 23, 1992, GB Appl. 91/40, Jan. 3, 1991>(Chem. Abstr., 1993, 118, 27464)

Murakami, Y.; Asakura, S.; Nakade, T. Manufacture of Sustained-release Pharmaceutical Microspheres. Jpn. Kakai Tokkyo Koho JP 04,360,825 [92,360,825], Dec. 14, 1992, Appl. No. 91/159,797, Jun. 3, 1991. (Chem. Abstr., 1993, 118, 154584)

Naplatanova, D.; Tyutyulkova, N.; Tomasini, L. Depoacetysal Tablets. Farmatsiya (Sofia), 1972, 22, 17–21. (Chem. Abstr., 1972, 76, 158288)

Narayanan, K. S.; Taylor, P. D. Sustained-release, N-Substituted Pyrrolidone Esters of Pharmaceuticals and Process for Their Use, U.S. Pat. No. 5,206,386 Apr. 27, 1993, application Ser. No. 675,367, Mar. 20, 1991. (Chem. Abstr., 1993, 119, 160092)

Nikolayev, A. S.; Gebre-Mariam, T. Preparation and Bioavailability Studies of Aspirin Ethyl Cellulose Microcapsules. Indian Drugs, 1993, 30, 392–397. (Chem. Abstr., 1993, 119, 210484)

Pinkus et al., J. Polym. Sci., Polym. Chem. Ed., 1984, 22, 1131–1140.

Plaizier-Vercammen, J. A.; Van den Bossche, H. Pharm. Ind., 1992, 54, 973–977. (Chem. Abstr., 1993, 119, 55854)

Ramstack, J. M.; Herbert, P. F.; Strobel, J.; Atkins, T. J.; Hazrati, A. M. Preparation of Biodegradable Microparticles Containing a Biologically Active Agent. PCT Int. Appl. WO 95 13,799, May 26, 1995, U.S. application Ser. No. 154,409, Nov. 19, 1993. (Chem. Abstr. 1995, 123, 179481)

Rehders, K.; Sinirock, R.; Spahn, H.; Mutschler, E.; Breddin, H. K. Plasma Salicylate Levels and Chronic Administration of Slow Release Acetylsalicylic Acid (Monobeltin). Eur. J. Clin. Pharmacol. 1985, 27, 683–687. (Chem. Abstr., 1985, 102, 172550)

Rettenmaier, J. Jr. Coated Cellulose Particles for Direct Drug Tableting. Ger. Offen. DE 4,121,127, Jan. 14, 1993. (Chem. Abstr., 1993, 118, 132173)

Roberts, M. S.; McLeod, L. J.; Cossum, P. A.; Vial, J. H. Eur. J. Clin. Pharmacol. 1984, 27, 67–74. (Chem. Abstr., 1985, 102, 12274)

Roseman, T. J.; Mansdorf, S. Z., eds. Controlled Release Delivery Systems, New York: Marcel Dekker, 1983.

Rosoff, M., ed. Controlled Release of Drugs: Polymers and Aggregate Systems, New York: VCH Publishers, 1989.

Sakauchi, N.; Kawakami, M. Sustained Release Pharmaceuticals. Jpn. Kokai Tokkyo Koho 79,154,515, Dec. 5, 1979, application Ser. No. 78,61,048, May 1, 1978. (Chem. Abstr. 1980, 92, 203591)

Schmitt et al., U.S. Pat. No. 3,422,871, 1969.

Schoen et al. (Ger. Offen. 1,917,738, Oct. 8, 1970; App. Apr. 5, 1969) Chem. Abstr., 1971, 74, 4375.

Schoen, N.; Pampus, G.; Schnoering, H. Embedding or Encapsulating Solid or Liquid Substances in Polymers Containing Carboxyl or Carboxylate Groups (Ger. Offen. 1,917,738, Oct. 8, 1970, Appl. Apr. 5, 1969. (Chem. Abstr., 1971, Sharma, C. P.; Paul, W. Poly(vinyl alcohol) Dialysis Membranes: Permeability Changes Due to Aspirin Release, Polym. Mater. Sci. Eng., 1992, 66, 495–496. (Chem. Abstr., 1993, 119, 80169).

Shell, J. W. Alkyl-substituted Cellulose-based Sustained-release Oral Drug Dosage Forms, PCT Int. Appl. WO 93 18,755. Sep. 30, 1993, U.S. application Ser. No. 858,320, Mar. 25, 1992. (Chem. Abstr., 1993, 119, 256550)

Stivic, I.; Senjkovic, R. Ion Exchangers and Sustained Release Action of Drugs, Acta Pharm. Jugosl. 1974, 24, 249–258. (Chem. Abstr., 1975, 82, 116048)

Streuff, B.; Puetter, J. Slow-release Acetylsalicylic Acid Oral Formulations. Ger. Offen. DE 3,346,571, Jul. 4, 1985, Appl. Dec. 23, 1983. (Chem. Abstr., 1985, 103, 129080)

Struszczyk, H.; Boldowicz, D. Conception of Microcrystalline Application as Polymeric Carriers for the Controlled Release of the Acetylsalicylic Acid. Cellul. Chem. Technol. 1986, 20, 201–207. (Chem. Abstr., 1986, 105, 48903)

Super, H. et al. Polymer Bull., 1994, 32, 509–515

Tanner, D. W.; Gardner, R. F. G. Polymeric Coating of Aspirin. Brit. 1,109, 425, Apr. 10, 1968, Appl. Jun. 16, 1964. (Chem. Abstr., 1968, 68, 107899)

Tarcha, P. J., ed. Polymers for Controlled Delivery, Boca Raton, Fla.: CRC Press, 1991.

Thanoo, B. C.; Sunny, M. C.; Jayakrishnan, A. Controlled Release of Oral Drugs from Crosslinked Polyvinyl Alcohol Microspheres. J. Pharm. Pharmacol. 1993, 45, 16–20. (Chem. Abstr., 1993, 118, 87566)

Thanoo, B. C.; Sunny, M. C.; Jayakrishnan, A. Oral Sustained-release Drug Delivery Systems Using Polycarbonate Microspheres Capable of Floating on the Gastric Fluid. J. Pharm. Pharmacol. 1993, 45, 21–24. (Chem. Abstr., 1993, 118, 87567)

Torrado, S.; Torrado, Susana; Torrado, V. J. "In Vitro" Drug Release of AAS Matrix Tablets, Proc. Int. Symp. Controlled Release Bioact. Mater., 20th 1993, 370–371; ed. by Roseman, T. J. et. al. Controlled Release Soc., Deerfield, Ill. (Chem. Abstr., 1993, 119, 278520)

Tu, X.; Mao, F.; Li, J. Sustained-release Aspirin Tablets. Nanjing Yaoxueyuan Xuebao 1986, 17, 107–112. (Chem. Abstr., 1986, 105, 102450)

Wang, D. P.; Tu, T. C.; Yeh, M. K. A Study of Slow-release Dosage Form (III), Zhonghua Yaoxue Zazhi, 1993, 45, 163–170. (Chem. Abstr., 1993, 119, 80099)

Wheatley, T. A.; Bridges, C. I., Jr.; Steuernagel, C. R. Film-forming Compositions for Coating Pharmaceuticals, U.S. U.S. Pat. No. 5,206,030, Apr. 27, 1993, application Ser. No. 484,309. Feb. 26, 1990. (Chem. Abstr., 1993, 119, 80229)

Wilson, C. G.; Parr, G. D.; Kennerly, J. W.; Taylor, M. J.; Davis, S. S..; Hardy, J. G.; Rees, J. A. Pharmacokinetics and In Vivo Scintigraphic Monitoring of a Sustained-release Acetylsalicylic Acid Formulation. Int. J. Pharm. 1984, 18, 1–8. (Chem. Abstr., 1985, 103, 180025)

Yanaihara, H.; Nakano, S.; Murakami, K.; Hukuda, T.; Ogawa, N. Pharmacokinetics of Acetylsalicylic Acid and Salicylic Acid from Slow-release Formulations of Aspirin in Healthy Japanese Volunteers. Rinsho Yakuri 1985, 16, 589–596. (Chem. Abstr., 1986, 104, 10520)

Yoles, S.; Sartori, M. F. In Controlled Rel. Technol. Methods Theory Applic. 1980, 2, p. 1. (Linhardt, see ref.)

It is understood that, given the directions provided herein, persons having skill in the art will, with no more than a reasonable amount of experimentation, be able to form complexes of other ester-rich polymers with other carboxyl-containing compounds.

What is claimed is:

1. A composition of matter useful for the slow release of a biologically active carboxyl-containing compound, the composition being formed by preparing a molten solution of a polyglycolide and a carboxyl-containing biologically active compound; and cooling said molten solution to form a complex of the polyglycolide and carboxyl-containing compound having a compound:monomeric unit ratio of at least about 1:1.

2. A complex formed by preparing a molten mixture of a polyglycolide and a carboxylic acid selected from the group consisting of acetylsalicylic acid, (S)-(+)4-isobutyl-α-methylphenylacetic acid, phenylacetic acid, phenoxyacetic acid, benzoic acid and salicylic acid; the complex having a carboxylic acid:monomer unit ratio of at least about 1:1.

3. A complex between a polyglycolide and a carboxyl-containing biologically active compound, in a ratio of carboxylate compound to momomeric polyglycolide unit of from about 1:10 to about 10:1.

4. An aspirin polyglycolide complex produced by preparing a molten mixture of aspirin and polyglycolide and solidifying said mixture.

5. A composition of matter comprising an aspirin-polyglycolide complex having an aspirin:monomeric ratio of at least about 1:1.

6. An aspirin polyglycolide complex having an aspirin:monomer ratio of at least about 1:1 and formed by melting a mixture of polyglycolide and aspirin.

7. The complex of claim 4 where the polyglycolide has monomeric units and the complex contains a monomeric unit:aspirin ratio of between about 1:10 and about 10:1.

* * * * *

UNITED STATES PATENT AND TRADEMARK OFFICE
CERTIFICATE OF CORRECTION

PATENT NO. : 5,855,915
DATED : January 5, 1999
INVENTOR(S) : A. George Pinkus

It is certified that error appears in the above-identified patent and that said Letters Patent is hereby corrected as shown below:

In claim 4, column 22, line 7, after 'aspirin', insert --:-- therefor.
In claim 5, column 22, line 10, delete "-", insert --:-- therefor.
In claim 6, column 22, line 13, after 'aspirin', delete "-".

Signed and Sealed this

Thirteenth Day of July, 1999

Attest:

Attesting Officer

Q. TODD DICKINSON

Acting Commissioner of Patents and Trademarks